United States Patent [19]
Barbera-Guillem et al.

[11] Patent Number: 6,126,835
[45] Date of Patent: *Oct. 3, 2000

[54] DEVICE AND METHOD FOR MAGNETIC SEPARATION OF BIOLOGICAL MOLECULES

[75] Inventors: Emilio Barbera-Guillem, Powell; Marlin O. Thurston, Columbus, both of Ohio

[73] Assignee: BioCrystal Ltd., Westerville, Ohio

[ * ] Notice: This patent is subject to a terminal disclaimer.

[21] Appl. No.: 09/240,811

[22] Filed: Feb. 1, 1999

Related U.S. Application Data

[63] Continuation-in-part of application No. 09/079,469, May 15, 1998.

[51] Int. Cl.[7] .............................. B01D 35/06; B03C 1/00; C12N 13/00

[52] U.S. Cl. .......................... 210/695; 210/222; 210/223; 209/213; 96/1; 435/2; 435/7.21; 435/173.1; 435/261; 435/803; 436/526; 436/824

[58] Field of Search ........................ 428/355 R; 210/222, 210/223, 695; 209/213; 96/1; 435/7.21, 2, 173.1, 261, 803; 436/526, 824

[56] References Cited

U.S. PATENT DOCUMENTS

| | | |
|---|---|---|
| 4,910,148 | 3/1990 | Sorensen et al. . |
| 5,078,871 | 1/1992 | McCready .............................. 210/222 |
| 5,663,241 | 9/1997 | Takamatsu et al. ................ 428/355 R |

*Primary Examiner*—David A. Reifsnyder
*Attorney, Agent, or Firm*—M. Bud Nelson

[57] ABSTRACT

Provided is a magnetic separation device comprising a container having one or more outer surfaces; at least one magnetic sheet; and a physical coupler that is used to detachably secure the container to the magnetic sheet. A method of using the magnetic separation device according to the present invention comprises obtaining a fluid containing a mixed population of biological molecules, from which it is desired to separate at least one subpopulation of biological molecules; mixing the fluid with a magnetic separation reagent; contacting the mixture with the fluid holding chamber of the magnetic separation device; incubating the mixture for a sufficient time to allow for complexes to form between the subpopulation of biological molecules and the magnetic separation reagent; positioning the magnetic separation device in a position that magnetically attracts the complexes towards the magnetic sheet, and thereby holds them in position in the container; and removing the remainder of the fluid from the magnetic separation device.

72 Claims, 8 Drawing Sheets

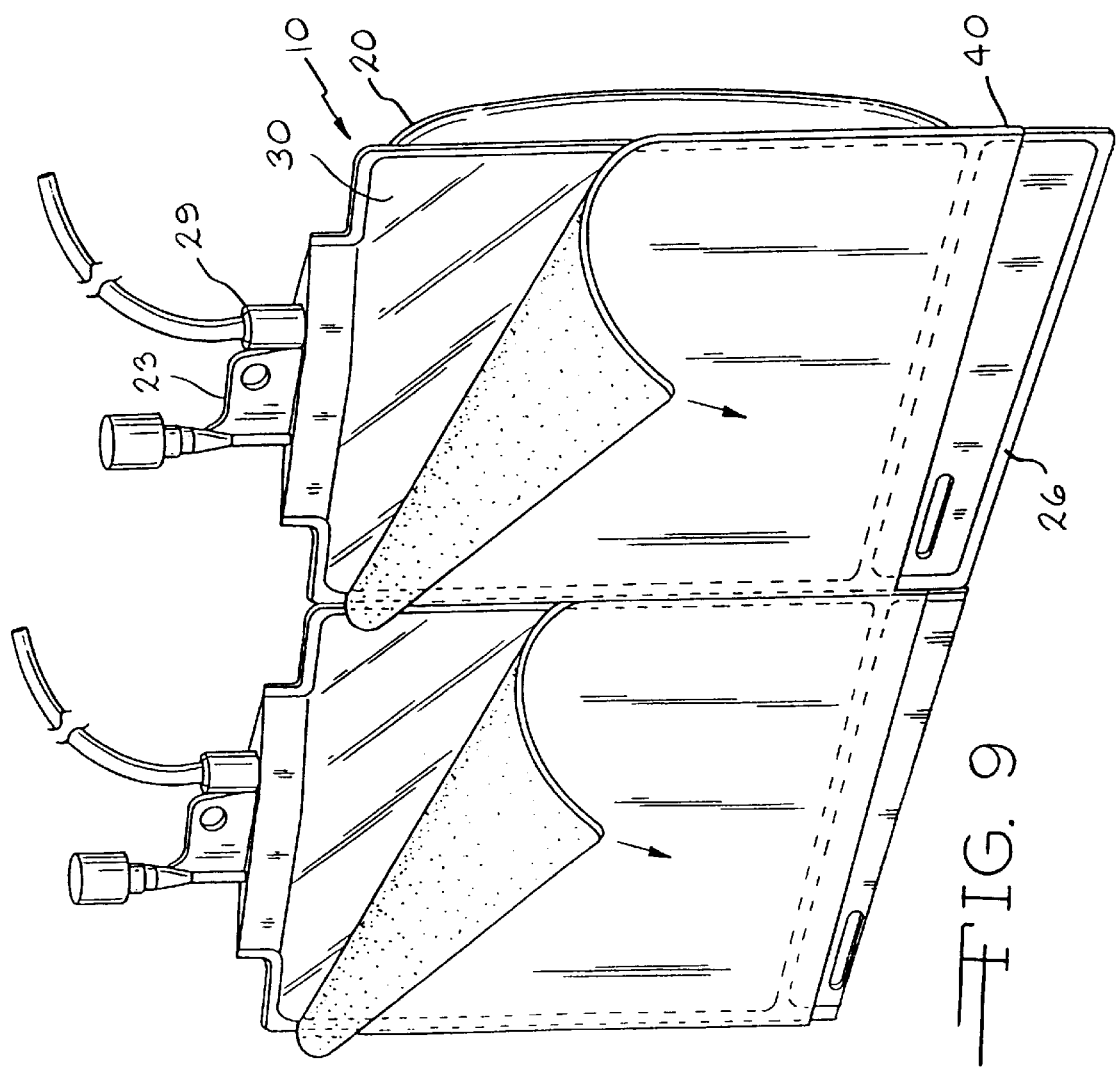

DEVICE AND METHOD FOR MAGNETIC
SEPARATION OF BIOLOGICAL
MOLECULES

This is a continuation-in-part application based on earlier co-pending application Ser. No. 09/079469 filed May 15, 1998 now allowed which is herein incorporated by reference.

FIELD OF THE INVENTION

The present invention generally relates to devices and methods for magnetic separation of one or more targeted molecules present in a solution comprising a mixed population of molecules. More particularly, the present invention relates to separation of target biological molecules using magnetic particles and a magnetic separation device.

BACKGROUND OF THE INVENTION

There are various methods available to isolate or separate biological molecules such as cells, antibodies, antigens, proteins, carbohydrates, nucleic acids, and the like. Magnetic separation techniques typically involve the application of a magnetic field to separate ferromagnetic particles contained within a fluid medium. Such techniques use devices that can be divided into two general types: an internal apparatus, or an external apparatus. In the internal apparatus, the ferromagnetic collection structure is contained within the fluid medium in order to intensify the applied magnetic field and improve the resultant gradient. One example of an internal apparatus involves packing steel wool or wires ("collection structures") into a column, wherein the column is situated adjacent to a magnet. A magnetic field is applied to the steel wires such that magnetic particles introduced into the column are attracted toward, and bind to, the steel wires. Another example of an internal apparatus involves loops of ferromagnetic wire that are inserted into a fluid medium. Drawbacks of such systems include entrapment of non-magnetic components; the potential for magnetic shielding of the collection structure therein; breakage of the collection structure during use and/or cleaning, and the requirement for cleaning or disposal of the collection structure between samples. In the external apparatus, generally the magnetic means is situated entirely externally with respect to the separation chamber. Typically, an external apparatus involves a plurality of magnets, or complex magnetic circuitry, placed around the periphery of the separation chamber; wherein the plurality of magnets, or the magnetic circuitry, produces a magnetic field gradient used to effect the magnetic separation. Drawbacks of the external systems include the need for intervention by the user to redesign the placement, positioning, or sizing of the plurality of magnets or circuitry to apply a magnetic field gradient to separation chambers of different sizes; and the additional need for manipulating multiple structures required for placement and positioning of the plurality of magnets or magnetic circuitry.

It is desirable, therefore, to provide a device for magnetic separation of components in a fluid that minimizes the amount of intervention necessary from a user. Additionally, it is desirable to provide a device for magnetic separation of components in a fluid that obviates the need for multiple structures for operation of the magnetic separation, and the manipulation associated with such structures.

SUMMARY OF THE INVENTION

It is an object of the present invention to provide a magnetic separation device that is simple to use, and provides a means for achieving rapid, high yield, and high purity of a selected biological molecule.

It is another object of the invention to provide a magnetic separation device that can be used to separate a biological molecule comprising a cell subpopulation of interest from a mixed population of cells in a fluid.

It is another object of the invention to provide a magnetic separation device that can be used to separately isolate more than one selected biological molecule of interest from a mixed population of biological molecules in a fluid. When the biological molecule comprises a cell subpopulation, the magnetic separation device may be used to separately isolate more than one cell subpopulation of interest from a mixed population of cells in a fluid.

It is further object of the invention to provide a magnetic separation device that may be available in a variety of sizes to provide an efficient and economical means for achieving rapid, high yield, and high purity of a selected biological molecule in a fluid.

It is an additional object of the invention to provide magnetic separation methods that are simple to use, and provide means for achieving rapid, high yield, and high purity of a selected biological molecule.

It is another object of the invention to provide magnetic separation methods that can separately isolate more than one selected biological molecule of interest from a mixed population of biological molecules in a fluid. When the biological molecule comprises a cell subpopulation, the magnetic separation methods may separately isolate more than one cell subpopulation of interest from a mixed population of cells (and/or non-cellular biological molecules) in a fluid.

According to one aspect of the invention, the magnetic separation device comprises a container having at least one side or face with an outer surface which is substantially flat, and to which outer surface is detachably secured in a face to face manner a magnetic sheet using a physical coupler. According to another aspect of the invention, a fluid containing a mixed population of biological molecules, and magnetic particles coated with a ligand (magnetic separation reagent) having sufficient binding specificity and affinity for the target biological molecule (the molecule desired to be isolated from the fluid) for achieving magnetic separation, are introduced into the container of the magnetic separation device. The magnetic separation reagent contacts and binds, via the ligand coating, with the target biological molecule present in the fluid in forming complexes. These complexes are drawn to, by magnetic attraction, and contact the inside of the face of container, the outer surface of which is detachably secured to the magnetic sheet. After a sufficient time for contact and binding interactions between the magnetic separation reagent and the target biological molecule in forming complexes, the fluid is removed thereby achieving either negative selection (wherein the separated target biological molecule is discarded) or positive selection (wherein the separated target biological molecule is to be retained). In positive selection, the inner surfaces of the container of the magnetic separation device may be washed to remove any remaining unbound biological molecules, while the target biological molecule remains bound, via magnetic attraction, as part of the complex with the magnetic separation reagent. A final fluid medium is introduced into the container, and the magnetic sheet is then removed from the container, thereby removing the magnetic force holding the complexes in place in the container and thereby releasing the complexes into the final fluid medium. The separated biological molecule may then be harvested from the complexes, if desired.

The above and other objects, features, and advantages of the present invention will be apparent in the following Detailed Description of the Invention when read in conjunction with the accompanying drawings in which reference numerals denote the same or similar parts throughout the several illustrated views and embodiments.

BRIEF DESCRIPTION OF THE DRAWINGS

FIG. 9 is a perspective view of an embodiment of a multiple unit of magnetic separation devices.

DETAILED DESCRIPTION OF THE INVENTION

Figure 1:
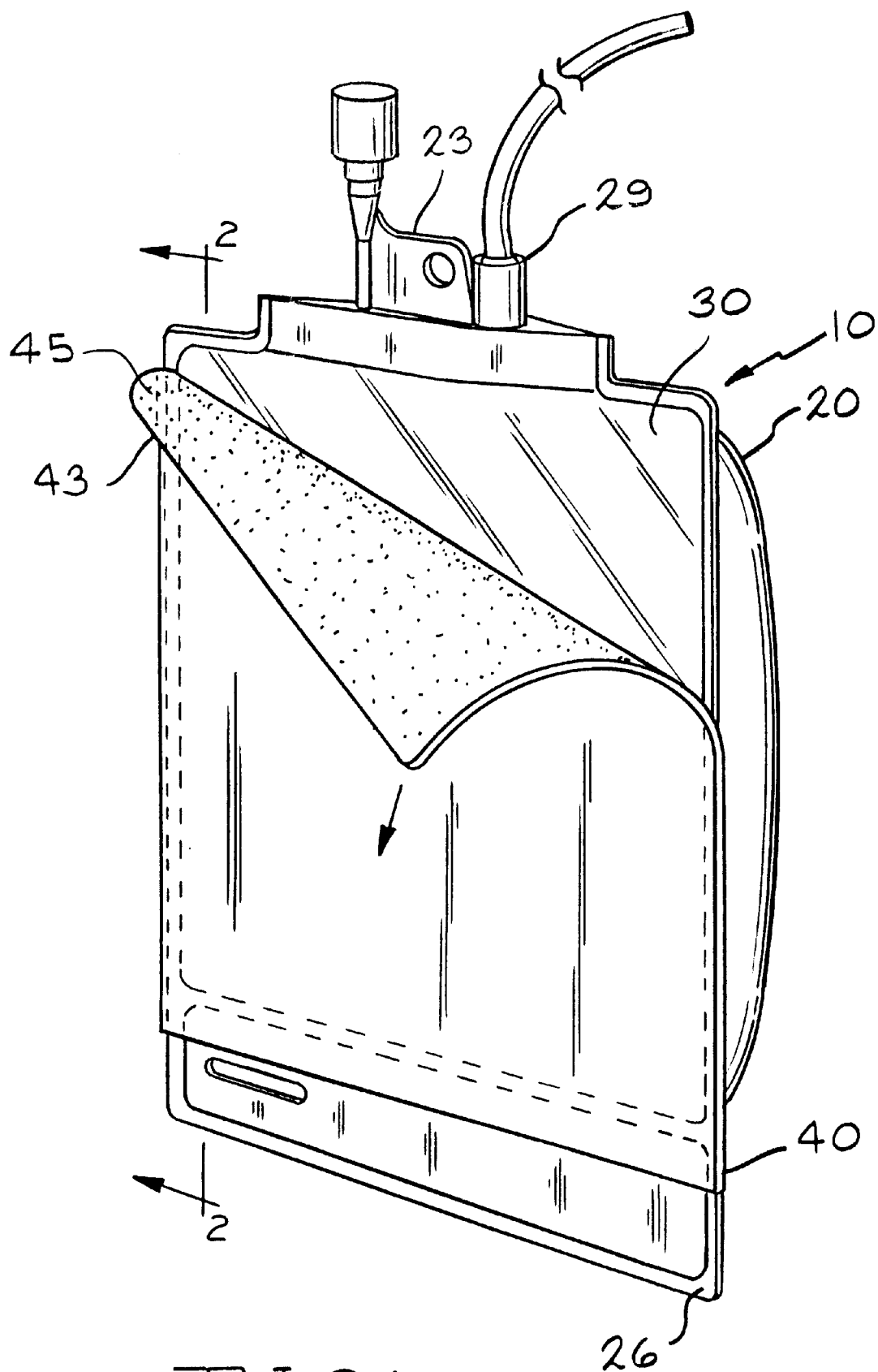
FIG. 1 is a perspective view of the magnetic separation device, wherein the magnetic sheet and the container are peeled apart to expose the non-permanent adhesive.

Definitions:

The term "biological molecule" is used herein, for purposes of the specification and claims, to mean a substance including, but not limited to, eukaryotic cells; prokaryotic cells; and complex molecules such as proteins, glycoproteins, lipoproteins, peptides, carbohydrates, lipids, nucleic acid molecules, and drugs. The term "ligand" when used in conjunction with a biological molecule is used herein, for purposes of the specification and claims, to mean a substance coating a magnetic particle which has binding specificity (to the substantial exclusion of other substances) and avidity for a biological molecule. Ligands are known to those skilled in the art to include antibodies, antibody fragments that retain binding activity (F(ab')$_2$, Fab', Fab, Fv, scFV, Fd' and Fd fragments); lectins; selectins; agglutnins; receptors (cell-associated or acellular); complementary nucleic acid sequences (e.g. anti-sense or oligonucleotide probes), aptamers, and other molecules which are capable of binding to a specific cell subpopulation or species of complex molecules. For example, and as known to those skilled in the art, a magnetic particle may be coated with a ligand that comprises a monoclonal antibody. Such a monoclonal antibody, when having binding specificity and avidity for a particular type of tumor cell (e.g., expressing a certain cell-associated tumor specific marker), can be used to bind substantially all cells of that particular tumor type (e.g., binding to cells expressing the tumor specific marker on their surface) that may be present in a fluid, thereby allowing for removal or isolation of that cell subpopulation from the fluid by magnetic separation. The term "magnetic separation reagent" is used herein, for purposes of the specification and claims, to mean magnetic particles coated with a specific ligand for the purpose of separating a specific subpopulation of ("target") biological molecule from a mixed population of biological molecules in a fluid using the device and method according to the present invention for magnetic separation.

The term "complexes" is used herein, for purposes of the specification and claims, to mean the magnetic separation reagent having bound thereto, via the ligand, target biological molecules.

The term "container" is used herein, for purposes of the specification and claims, to mean a chamber for holding a fluid, wherein the chamber has at least one wall having one or more inner surfaces and one or more outer surfaces; and at least one aperture which is closable or sealable to prevent the contents inside the container from leaking out of the container. The at least one aperture comprises one or more of: an inlet to allow for the introduction of one or more substances into the container; an outlet for withdrawal or removal of one or more substances from the container; a combination of an inlet and outlet; and a venting port for releasing air from the chamber as sample is introduced into the chamber. The container may be in the form including, but not limited, to a flexible bag ("bag"), such as a medical fluid bag, cell culture bag, or blood collection bag; a flask or bottle or roller bottle, such as for collecting medical specimens or culturing cells; and a chamber formed by sealing the material comprising at least two walls by or within a frame or solid support, as will be more apparent in the following embodiments. The magnetic separation device may have one or more openings set apart from the chamber, from which the magnetic separation device may be hung using a hook or other appropriate hanging means. The composition of the container may be of a thermoplastic polymer, of high ethylene vinyl acetate polymer content, a flexible synthetic resin, thin film membrane, gas-permeable membrane, or other suitable material having properties compatible with its intended purpose. In a preferred embodiment, at least one wall of the container is comprised of a gas-permeable membrane. Flexible bags are known in the art to be made of materials such as polyvinyl chloride, polyolefins (e.g., polyethylene), polyurethanes, and the like. In a preferred embodiment of the invention, the container is comprised of a material sufficiently clear enough to allow a user to visually observe the contents of the container, and manipulations of the contents therein.

The term "magnetic sheet" is used herein, for purposes of the specification and claims, to mean at least one substantially flat sheet having a magnetic field of sufficient strength to attract, and securedly hold into position, magnetic particles or magnetic separation reagent or complexes placed adjacent thereto. The magnetic sheet may be substantially stiff (including various degrees of stiffness as known to those skilled in the art), in which case a detachably secured container may be removed by pulling the container apart from the magnetic sheet; or may comprise a flexible magnetic sheet of a sufficient pliability to allow for the magnetic sheet of the magnetic separation device to be separated from the container by pulling the magnetic sheet apart from the container, as will be more apparent from the following examples. The magnetic sheet may be opaque, or transparent, depending on its composition. A magnetic sheet includes, but is not limited to, a sheet consisting of a fine magnetic powder such as barium ferrite loaded into a thermoplastic binder; a sheet of plastics or vinyl material impregnated with a ferromagnetic material; a sheet of synthetic resin material having mixed therein a magnetic powder; magnetic particles embedded in a polymer sheet of typically 0.7 mm or 0.030 inches thickness; a vinyl material including magnetic materials dispersed therethrough; or other suitable material having properties compatible with its intended purpose. As apparent to those skilled in the art, the thickness of the magnetic sheet will vary depending on factors which include, but are not limited to, the composition of the sheet material, whether the magnetic sheet comprises one or more sheets, the desired field strength, and the spacing of the magnetic poles. In that regard, and for purposes of illustration but not limitation, the thickness of the magnetic sheet may range from about 0.2 mm to about 5 mm. Illustrative examples of magnetic sheets that can be commercially purchased, and that are useful in making the magnetic separation device according to the present invention, are available under the trademark "PROMAG" (a strontium ferrite-based material) from Magnetic Specialty, Inc., Marietta, Ohio; and a bonded material comprising neodimium, iron, and boron from Electrodyne Co., Inc., Batavia, Ohio. Commercially available examples of a magnetic sheet have a magnetic field strength, as measured by a gaussmeter, in a range which includes, but is not limited to, about 150 to about 600 Gauss.

The term "magnetic particle" is used herein, for purposes of the specification and claims, to mean particles known in the art currently or in the future, which can be used to achieve magnetic separation by responsiveness and attraction to a magnetic field. Magnetic particles, also known in the art as magnetic spheres or magnetic beads or microclusters, comprise one or more compounds including, but not limited to, a core comprising one or more metals, metal oxides, metal alloys, metal salts, metal organic particles, metal hydroxides, and mixed lattices thereof. Inorganic cores are known in the art to be comprised of iron, cobalt, nickel, ferric oxide, nickel oxide, cobaltic oxides, and ferrites. Additionally, the magnetic particle may also be comprised of a polymeric coating for attachment to biological materials, a biodegradable coating, and/or another functional type of coating that may be useful or advantageous in magnetic separation. Biodegradable coatings on magnetic particles are known to those skilled in the art (for a review, see, e.g., U.S. Pat. No. 5,707,877; U.S. Pat. No. 5,382,468).

The term "physical coupler" is used herein, for purposes of the specification and claims, to mean a device or structure or substance that promotes (either by itself, or in conjunction with forces resulting from fluid added into the container) intimate, physical contact between the container of the magnetic separation device and the magnetic sheet of the magnetic separation device sufficient (a) to detachably secure the magnetic sheet and container together thereby forming an assembled unit comprising the container, the magnetic sheet and the physical coupler, and wherein the assembled unit comprises the magnetic separation device; and (b) for magnetic particles placed within the container to be attracted to, and held into position (along the surface of the container adjoining the magnetic sheet) by, the magnetic field strength of the detachably secured magnetic sheet. The physical coupler may comprise a support structure, one or more frames, one or more fasteners, one or more clamps, a non-permanent adhesive, a sealed vacuum hold-down, a ferromagnetic material to which the magnetic sheet can bind via magnetic attractive forces, or other suitable form having properties compatible with its intended purpose, as will be more apparent to one skilled in the art from the following description.

The term "non-permanent adhesive" is used herein, for purposes of the specification and claims, to mean a "removable" adhesive of a sufficiently low tack that allows the magnetic sheet of the magnetic separation device according to the present invention to be removed from the container, as will be more apparent from the following embodiments. That is, the non-permanent adhesive is an adhesive of adequate peel strength to allow for the magnetic sheet to be pulled apart from the container, without substantially damaging surfaces of either the container and magnetic sheet when they are pulled apart from each other. Further, the adhesive is of an initial and appropriate cohesive strength to control and inhibit the substantial transfer of adhesive residue to a surface other than the surface onto which it is specifically layered. The non-permanent adhesive may be in the form of a double-faced adhesive tape, a polymeric adhesive, a pressure-sensitive acrylic adhesive, hot-melt adhesive, rubber cement, or any other form of adhesive useful for the purposes attendant to the present invention, as will be more apparent in the following descriptions. Double-faced adhesive tapes are known in the art to have adhesives on both sides of a film or carrier, wherein the film or carrier functions as a support onto which is applied the adhesives.

In a preferred embodiment, the non-permanent adhesive comprises a "repositionable" adhesive which allows for the magnetic sheet to be removed from the container; and additionally if desired, following removal, allows for the magnetic sheet to be repositioned with respect to the container, and re-applied in a detachably secured manner with the application of light pressure to the container and/or magnetic sheet. Repositionable adhesives can be repeatedly adhered to and removed from a substrate without substantial loss of adhesion capacity (for a review of such adhesives, see, e.g., U.S. Pat. No. 5,663,241). Illustrative examples of a high performance pressure sensitive adhesives useful in making the magnetic separation device according to the present invention are commercially available under the product name "MACbond IB-3628" by MACtac, Inc., Stow, Ohio; and AR-7840 by Adhesives Research, Inc.

EXAMPLE 1

In this example, illustrated are various embodiments of the magnetic separation device according to the present invention.

In its simplest form, the magnetic separation device 10 of the present invention is comprised of three main components, as illustrated in FIGS. 1–5, and 8. The magnetic separation device 10 comprises a container 20 having at least one face or side 30, the outer surface of face 30 being substantially flat. Container 20 is removably attached to magnetic sheet 40 by a physical coupler 45. In one illustration of this embodiment, the physical coupler 45 comprises non-permanent adhesive 45. That is, non-permanent adhesive 45 may be applied to and form a coat on a surface selected from the group consisting of an outer surface of side 30 of container 20 (see, e.g., FIGS. 3 & 4), a face 43 of magnetic sheet 40 to be engaged by side 30 (see, e.g., FIGS. 1 & 5), or a combination thereof. To the outer surface of side 30 is detachably secured over a substantial area of side 30 a magnetic sheet 40 such that container 20 and magnetic sheet 40 meet in a face to face manner in being assembled together to form magnetic separation device 10. In another illustration of this embodiment, the magnetic separation device comprises a frame, comprising two frame pieces, which: (a) helps to form the container; (b) facilitates the magnetic sheet to come in physical contact with the container; and (c) is part of, and provides structural support to, the magnetic separation device (see, e.g., FIGS. 6, 7A, and 7B). In another embodiment, the magnetic separation device comprises a container which is removably attached to the magnetic sheet by a physical coupler, and further comprises a backing plate which is placed in physical contact with the magnetic sheet on the side of the magnetic sheet opposite to that where the container is detachably secured (see, e.g., FIG. 7B).

Typically, the magnetic separation device will comprise a single unit. However, also encompassed herein by the term "magnetic separation device" is a magnetic separation device that is part of a multiple unit. As illustrated in FIG. 9 by way of example, the multiple unit may comprise a plurality of magnetic separation devices which are physically connected in tandem, but which may be manipulated to maintain a separate chamber per magnetic separation device. Regarding the multiple unit, each magnetic separation device thereof may comprise a magnetic sheet of the same field strength. In another embodiment, a first magnetic separation device of the multiple unit may have a magnetic sheet field strength which is different than the field strength of the magnetic sheet of a second magnetic separation device of the multiple unit. Variations in the magnetic field strength between magnetic separation devices may be used to selectively attract and hold into place magnetic particles of different size. For example, a magnetic separation device having a magnetic sheet with a low field strength (e.g., 150 to 200 Gauss) may preferentially attract and hold into place magnetic separation reagents comprising larger magnetic particles than a magnetic separation device having a magnetic sheet with a higher field strength (e.g., 400 to 500 Gauss) that may preferentially attract and hold into place magnetic separation reagents comprising smaller particles. In that regard, a two-to-one difference in size of a magnetic particle may result in about an eight-to-one difference in the strength of attraction to a given magnetic field. Hence, a differential separation, based on magnetic particle size and magnetic sheet field strength, may be achieved using such a multiple unit.

Alternatively, a multiple unit may comprise a magnetic separation device physically connected to a plurality of containers. The series of containers are physically connected in tandem, and may be manipulated to maintain a separate chamber per container. The magnetic sheet may be removed from a first magnetic separation device of the multiple unit, after a first selection process, and applied (by means of a physical coupler) and detachably secured to one of the containers in the plurality of containers to form a second magnetic separation device for a second selection process. Thus, the same magnetic sheet may be applied to, and may be used for, each container of the plurality of containers. The multiple unit, may also have at least one separate aperture specific for each respective container in the multiple unit.

EXAMPLE 2

In this example, further illustrated are various embodiments of the magnetic separation device according to the present invention. In the embodiment shown in FIG. 1, container 20 comprises a bag capable of holding a fluid. Examples of such bags include, but are not limited to, blood collection bags, cell culture bags, or medical solution bags. Because a conventional assortment of such bags are used by those skilled in the art, wherein the assortment of bags differ in size and therefore fluid capacity as well as overall length and width, it will be appreciated, of course, that the dimensions of bag 20 represented in FIGS. 1–4, and others which are subsequently given herein, are merely for purposes of explanation and illustration, and are not intended to limit the invention in any way. For example, standard or conventional sizes of such bags include a size for fluid capacities ranging from approximately 30 ml to approximately 100 ml; a size for fluid capacities ranging from approximately 150 ml to approximately 500 ml, and a size for fluid capacities ranging from approximately 300 ml to 1500 ml. However, custom size bags (e.g., for fluid capacities for less than 1 ml, and between 1 ml and 30 ml) can be easily manufactured using methods and materials known to those skilled in the art; and such custom size bags may be used with the present invention.

In a preferred construction, bag 20 comprises a walled housing means with at least one aperture 29 through which a fluid may be introduced into, and/or removed from, bag 20. Bag 20 has a side or face 30 the outer surface of which is substantially flat. Detachably secured over a substantial means of the outer surface of face 30 is magnetic sheet 40, such that bag 20 and magnetic sheet 40 meet in a face (30) to face (43) manner in being assembled together to form magnetic separation device 10. The magnetic sheet 40 and the side 30 of bag 20 to which it is detachably secured may generally, but not necessarily, be dimensionally coextensive in length, width, and shape. In a preferred embodiment, magnetic sheet 40 is flexible, and is generally dimensionally coextensive in length, width, and shape with that section of bag 20 along side 30 which comprises the fluid holding chamber of bag 20; thereby maximizing the functional surface area along side 30 available for magnetic separation reagent and/or complexes to bind. In a preferred embodiment, when the container is a bag, a portion of the bag 20 extends beyond the dimensional margins of the magnetic sheet 40 such that the user can readily grip the extended portion of the bag 20 to start the peeling action when it is desired to separate the bag from the magnetic sheet, as shown in FIGS. 1–4. For example, one standard size for a bag having a fluid capacity of approximately 30 to 60 ml is about 6 inches in width (side to side) and 8 inches in height (top 23 to bottom 26).

In continuing with this example, and with reference to FIG. 1, a magnetic sheet 40 of about 6 inches in width and 6 inches in height is detachably secured to bag 20 so as to be generally dimensionally coextensive in length, width, and shape (with the fluid holding chamber of bag 20). With continuing reference to FIG. 1, physical coupler 45, comprising a non-permanent adhesive, is applied to, and forms a coat on, surface 43 of magnetic sheet 40. Pressure is applied to bag 20 and/or magnetic sheet 40 where they are dimensionally coextensive in detachably securing bag 20 to magnetic sheet 40 in a face to face manner thereby forming magnetic separation device 10 (see also, FIG. 2). FIG. 1 shows the magnetic sheet 40, comprising a flexible magnetic sheet, being pulled apart from bag 20 (see arrow) as would be performed in the method of using magnetic separation device 10 when it is desired to release complexes formed therein. Additionally, FIG. 1 shows the magnetic sheet 40 being pulled apart (e.g., peeled away) from bag means 20 (see arrow) for the additional purpose of showing physical coupler 45, comprising a non-permanent adhesive, as applied to, and remaining substantially bonded to, face 43 of magnetic sheet 40.

Figure 3:
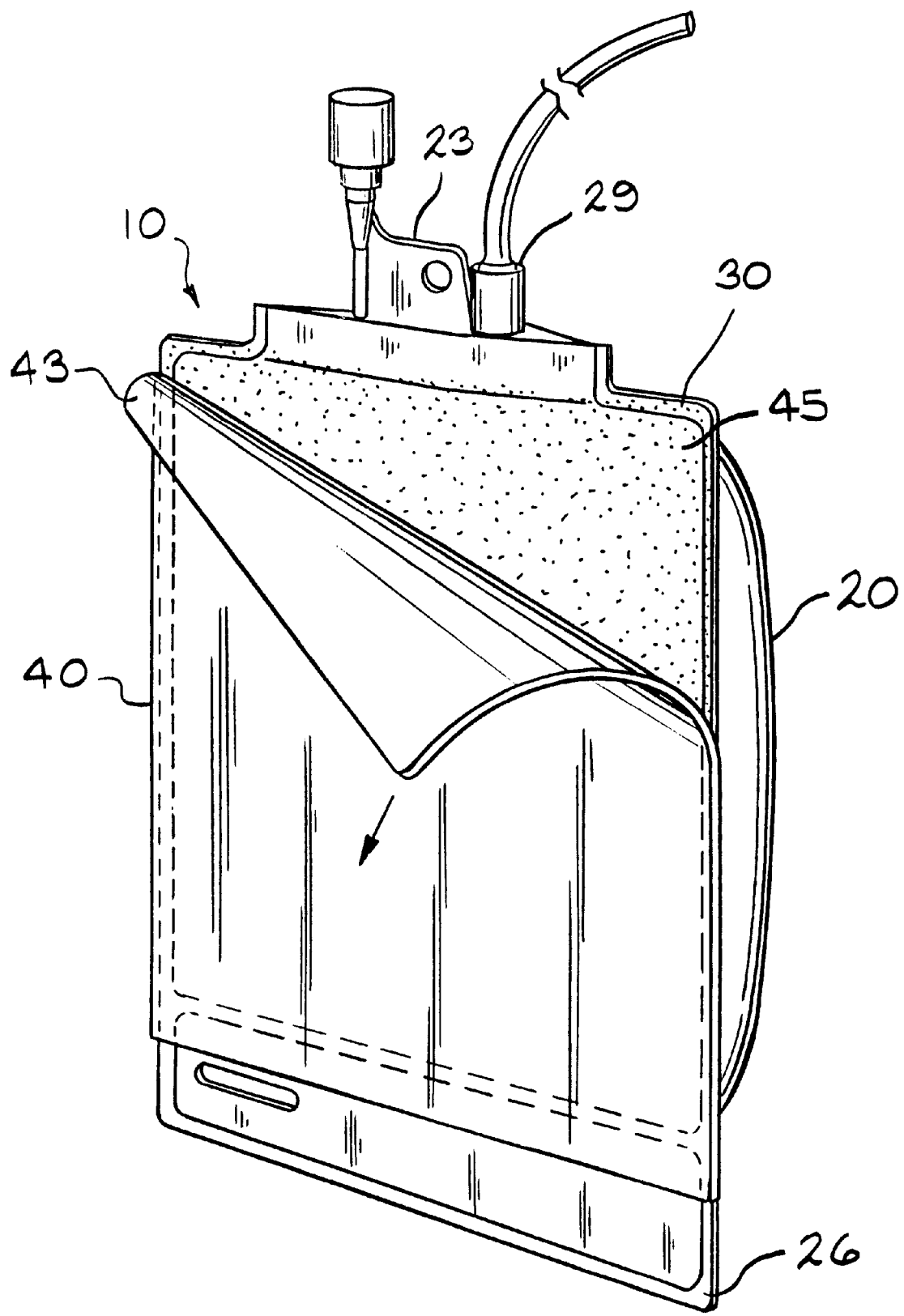
FIG. 3 is a perspective view of another embodiment of the magnetic separation device, wherein the flexible magnetic sheet and the container are peeled apart to expose the non-permanent adhesive.

In an additional preferred construction as illustrated in FIG. 3, the bag 20 comprises a walled housing, with a chamber for holding fluid, and with at least one aperture 29 through which a fluid may be introduced into, and/or removed from, bag 20. Bag 20 has a side or face 30 the outer surface which is substantially flat. Detachably secured over a substantial portion of the outer surface of face 30, is magnetic sheet 40 such that bag 20 and magnetic sheet 40 meet in a face (30) to face (43) manner in being assembled together to form magnetic separation device 10. The magnetic sheet 40 and the side 30 of bag 20 to which it is detachably secured may be generally dimensionally coextensive in length, width, and shape (especially in relation with the fluid holding chamber of bag means 20). Bag 20 may, but does not necessarily have to, extend beyond the dimensional margins of the flexible magnetic sheet 40 such that the user can readily grip the extended portion of the bag 20 to start the peeling action (see arrow) when it is desired to separate bag 20 from the magnetic sheet 40. For example, a standard size for a bag having a fluid capacity of between 100 ml to 150 ml is about 9 inches in width (side to side) and about 10 inches in height (top 23 to bottom 26).

Figure 4:
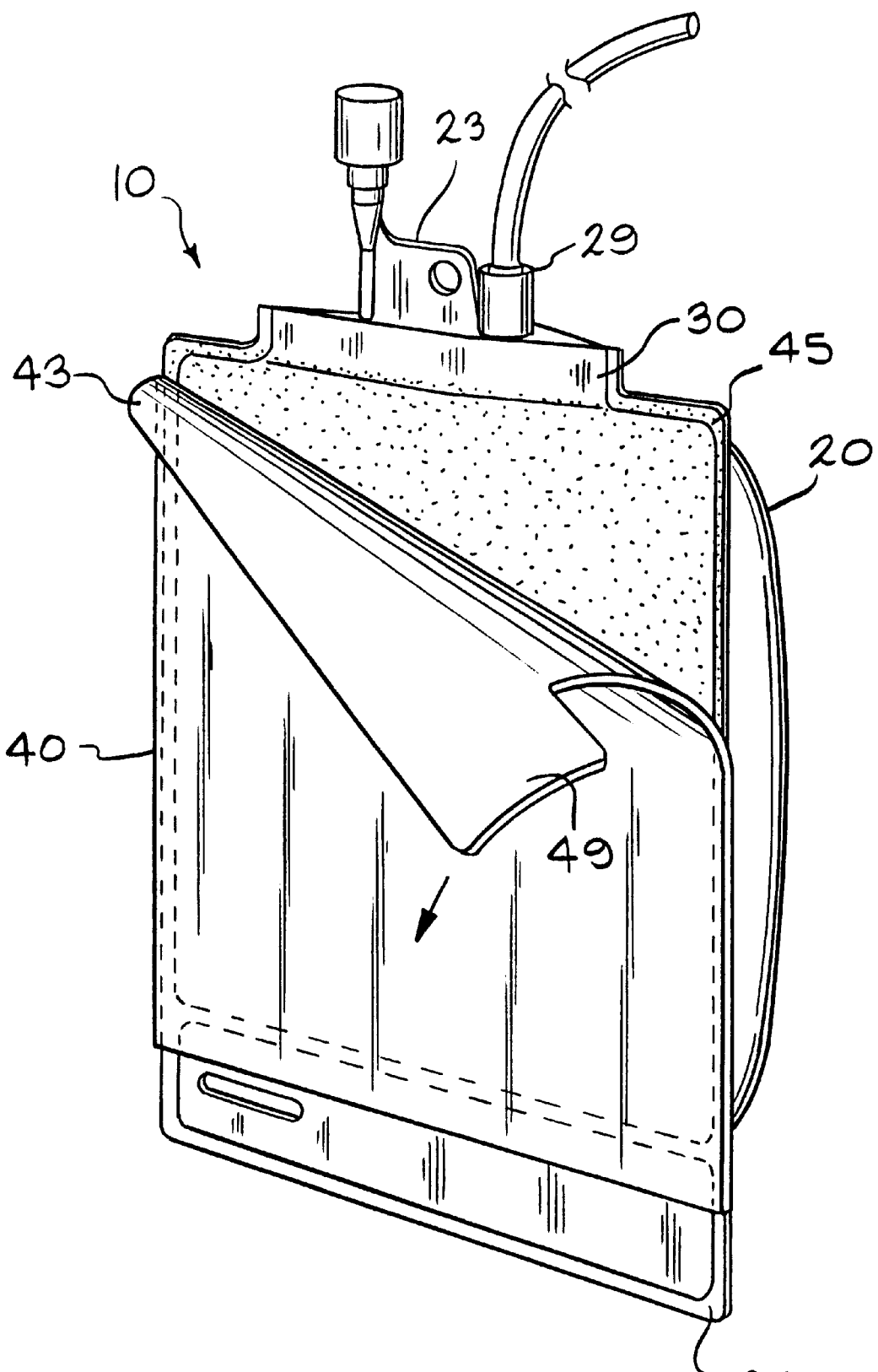
FIG. 4 is a perspective view of an additional embodiment of the magnetic separation device, wherein the flexible magnetic sheet with tab is pulled away from the container to expose the non-permanent adhesive.
Figure 8:
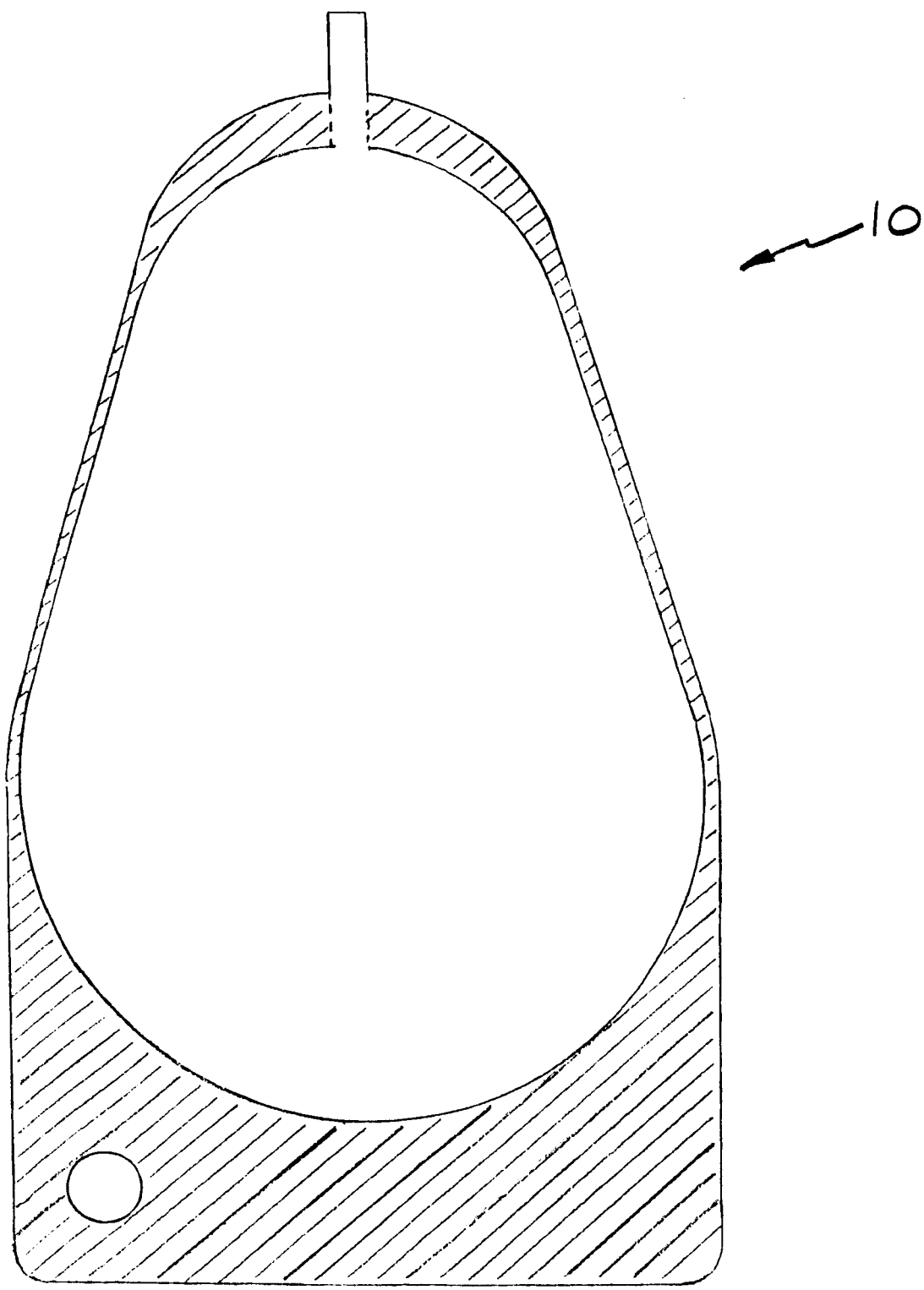
FIG. 8 is a front view of a magnetic separation device according to the present invention.

In continuing with this example, and with reference to FIG. 3, a magnetic sheet 40 of about 9 inches in width and about 9 inches in height can detachably secured to bag means 20 so as to be generally dimensionally coextensive in length, width, and shape; particularly in relation to the fluid holding chamber of bag 20. With continuing reference to FIG. 3, physical coupler 45, comprising a non-permanent adhesive, is applied to, and forms a coat on, surface 30 of bag 20. Pressure is applied to bag 20 and/or magnetic sheet 40 where they are dimensionally coextensive in detachably securing bag 20 to magnetic sheet 40 in a face to face manner thereby forming magnetic separation device 10. FIG. 3 shows magnetic sheet 40, as comprising a flexible magnetic sheet, being pulled apart from bag 20 (see arrow) as would be performed in the method of using magnetic separation device 10 when it is desired to release complexes formed therein. Additionally, FIG. 3 shows magnetic sheet 40 being peeled away from bag means 20 (see arrow) for the additional purpose of showing physical coupler 45, as comprising a non-permanent adhesive, as applied to, and remaining substantially bonded to, face 30 of bag 20. FIG. 4 illustrates an embodiment similar to the magnetic separation device illustrated in FIG. 3. However, magnetic separation device 10, as illustrated in FIG. 4, comprises magnetic sheet 40 having a radially projecting portion, such as tab means 49, so that the user can readily grip radially projecting tab 49 to facilitate pulling apart or disengaging magnetic sheet 40 from bag 20 by the application of a relatively small force in utilizing a "peeling" action (see arrow) when it is desired to separate magnetic sheet 40 from bag 20. FIG. 8 illustrates an embodiment similar to the magnetic separation device illustrated in FIGS. 1–4. However, magnetic separation device 10, as illustrated in FIG. 8, comprises a chamber with rounded corners, and wherein the rounded corners may minimize any possible trapping of fluid and/or cells such as could potentially happen in an angled corner.

Figure 7A:
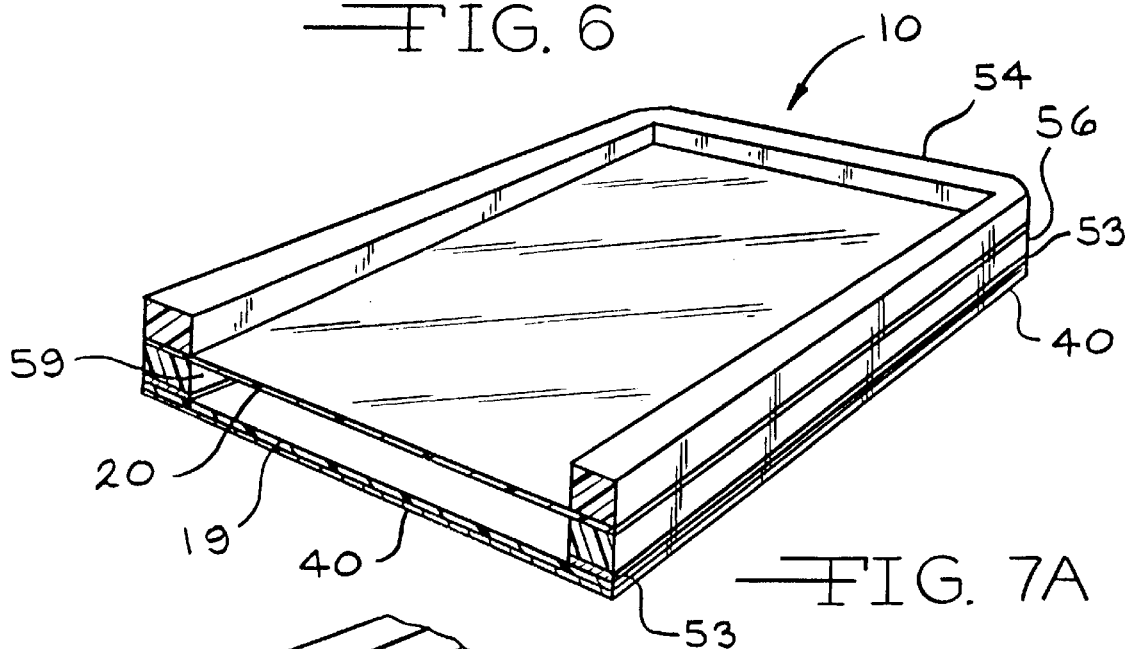
FIG. 7A is a partial perspective view, in cross-section, of a magnetic separation device, showing a magnetic sheet in relation to the container, which are contacted together using a physical coupler.
Figure 7B:
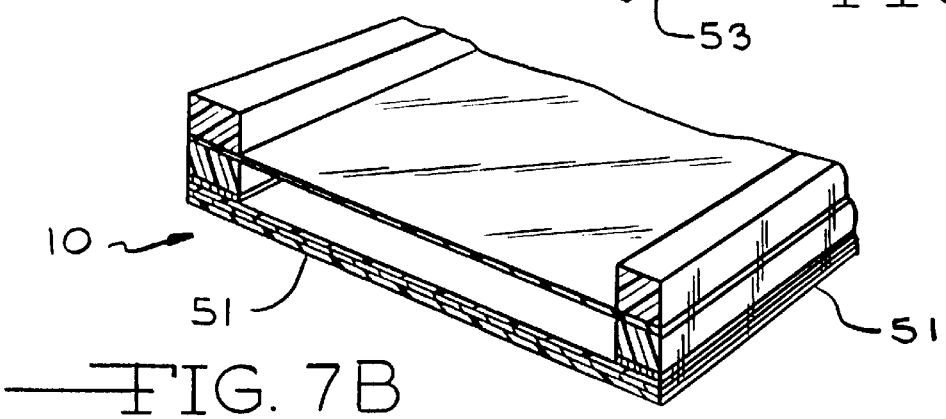
FIG. 7B is a fragmentary partial perspective view, in cross-section, of a magnetic separation device, showing a magnetic sheet in relation to the container, which are contacted together using a physical coupler, and further includes a metal backing plate.

In a variation of the embodiments illustrated in FIGS. 1–4, and 8 the magnetic separation device further comprises a backing plate which is placed in physical contact with the magnetic sheet on the side of the magnetic sheet opposite to that where the container is detachably secured (see, e.g., FIG. 7B as an illustration of placement position). In this embodiment, the backing plate comprises a sheet of ferromagnetic material that is held into position and contact with the magnetic sheet by the field strength of the magnetic sheet. Such ferromagnetic materials are known to those skilled in the art to include, but are not limited to, a sheet of iron, a sheet of an iron-containing alloy, or a sheet of silicon steel. In a preferred embodiment of utilizing a backing plate, the backing plate may generally, but not necessarily, be dimensionally coextensive in length, width, and shape with the magnetic sheet of the magnetic separation device. The backing plate may provide advantageous features to the function of the magnetic separation device. For example, the backing plate may add to the ease of handling the magnetic separation device by adding to the structural support of the magnetic separation device, and by providing a substantially flat surface for contacting a table or shaker incubator or other support surface. Such additional structural support may facilitate the use of a rack into which is placed the magnetic separation device substantially in a vertical position so that the user need not be required to hold the magnetic separation device when filling or otherwise manipulating the magnetic separation device. Additionally, a backing plate, when in such contact with the magnetic sheet, may significantly increase the field strength of the magnetic sheet as encountered by magnetic particles in the container. That is, the field strength of the magnetic sheet, on the side opposite to the adjoined backing plate, has been measured by a gauss meter to increase approximately 1.5 to 2 fold when the backing plate is adjoined (e.g., 478 Gauss) as compared to when there is no backing plate present (e.g., 316 Gauss).

Figure 5:
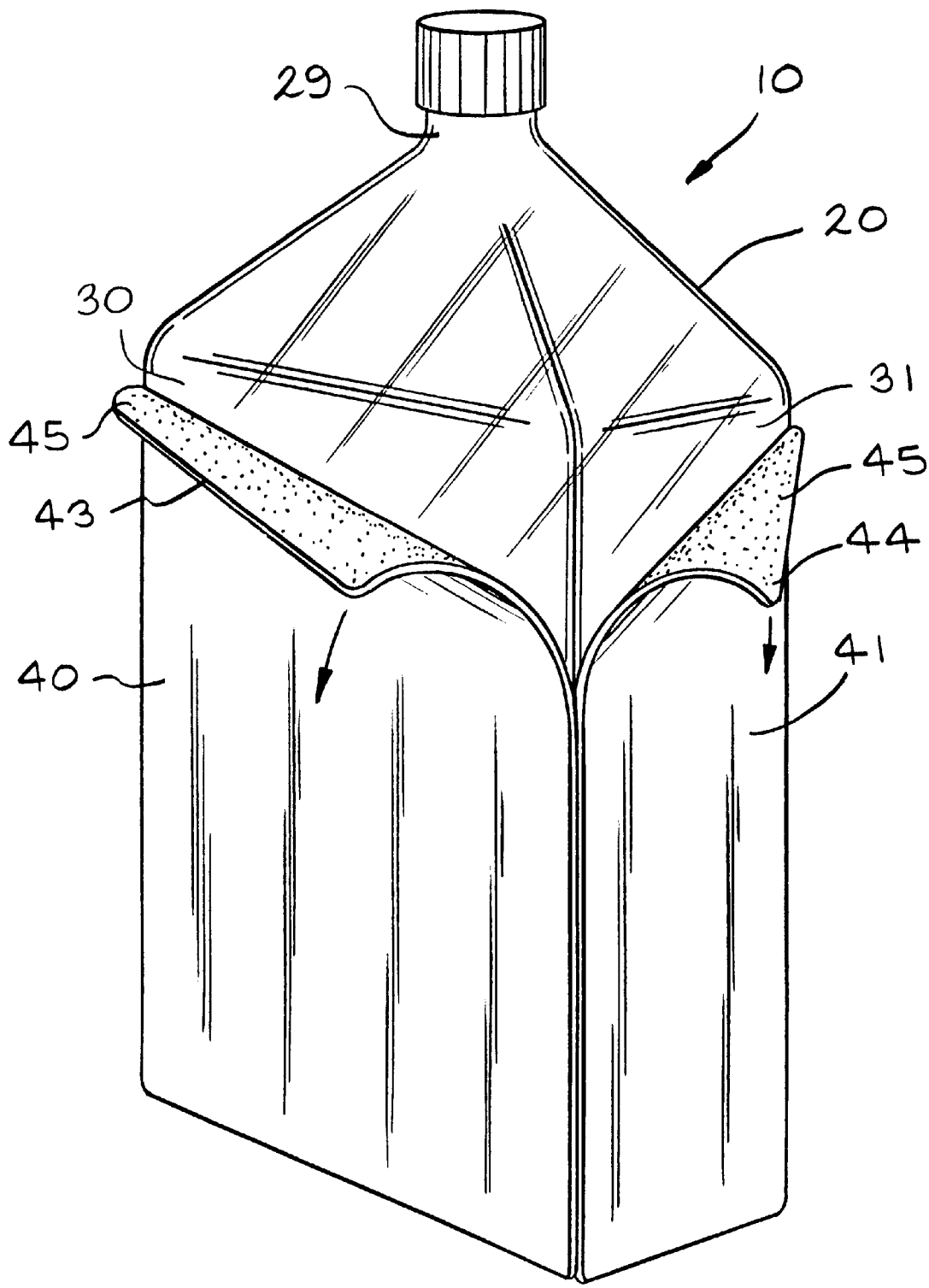
FIG. 5 is a perspective view of the magnetic separation device, showing multiple magnetic sheets in relation to the container, which are peeled apart to expose the non-permanent adhesive.

In a further preferred construction as illustrated in FIG. 5, magnetic separation device 10 comprises a container detachably secured to at least one magnetic sheet by a physical coupler. In this embodiment, the container can either be a bag or bottle. Importantly, depending on the number of sides of the container, multiple magnetic sheets may be detachably secured to the container (e.g., at least one magnetic sheet per side of the container) thereby allowing for multiple magnetic separations to be performed as will be more apparent in the following embodiments. With further reference to FIG. 5, container is a bottle 20 comprising a walled housing means with a chamber for holding fluid, and with at least one aperture 29 through which a fluid may be introduced into, and/or removed from, bottle 20. Bottle 20 has one or more sides or faces 30 and 31, the outer surfaces of which are substantially flat. Detachably secured over a substantial portion of each of the outer surfaces of faces 30 and 31 are magnetic sheets 40 and 41 such that bottle 20 and magnetic sheets 40 and 41 meet in a face to face manner in being assembled together to form magnetic separation device 10. The magnetic sheet 40, and side 30 of bottle 20 to which it is detachably secured, may generally be dimensionally coextensive in length, width, and shape; particularly in relation to the fluid holding chamber of bottle 20. The magnetic sheet 41, and side 31 of bottle 20 to which it is detachably secured, may generally be dimensionally coextensive in length, width, and shape; particularly in relation to the fluid holding chamber of bottle 20 along sides 30 and 31. Bottle 20 may, but does not necessarily have to, extend beyond the dimensional margins of the magnetic sheets 40 and 41, thereby allowing a user to readily grip the flexible magnetic sheets 40 and 41 to start the pulling action (see arrow) when it is desired to separate bottle 20 from either or both of the magnetic sheets 40 and 41.

In continuing with this example, magnetic sheets 40 and 41 comprise flexible magnetic sheets, and are detachably secured to bottle means 20 so as to be generally dimensionally coextensive in length, width, and shape, in forming magnetic separation device 10. A physical coupler, comprising a non-permanent adhesive, may be applied to and form a coat on a surface selected from the group consisting of an outer surface (30 and/or 31) of bottle 20, a face of the magnetic sheet (43 and/or 44), or a combination thereof. With continuing reference to FIG. 5, non-permanent adhesive 45 is applied to, and forms a coat on, face 44 of magnetic sheet 41; and is applied to, and forms a coat on, face 43 of magnetic sheet 40. Pressure is applied along the dimensions of magnetic sheets 40 and 41 in detachably securing bottle means 20 to magnetic sheets 40 and 41 in a face to face manner thereby forming magnetic separation device 10. FIG. 5 shows magnetic sheets 40 and 41 being pulled away and apart from bottle means 20 (see arrows) as would be performed in the method of using magnetic separation device 10 when it is desired to release complexes formed therein. Additionally, FIG. 5 shows magnetic sheets 40 and 41 being pulled away from bottle means 20 (see arrows) for the additional purpose of showing non-permanent adhesive 45 as applied to, and remaining substantially bonded to, face 43 of magnetic sheet 40, and face 44 of magnetic sheet 41.

It will be apparent to those skilled in the art from the descriptions herein that various modifications can be made of the embodiment illustrated in FIG. 5. For example, since bottle 20 has four main sides, the number of magnetic sheets that may be detachably secured to bottle 20 may range from one to four, depending on whether multiple magnetic separations are to be performed, and how many magnetic separations are to be performed, using the magnetic separation device. If the container contains more than 4 main sides, then it will be appreciated by those skilled in the art that the number of magnetic sheets that may be detachably secured to container 20 may range from 1 to greater than 4. Additionally, any of such one or more magnetic sheets being detachably secured to bottle 20 may have a radially projecting portion, such as a tab, so that the user can readily grip the radially projecting tab to facilitate pulling apart or disengaging the magnetic sheet from bottle 20 by the application of a relatively small force in utilizing a "peeling" action when it is desired to separate the magnetic sheet from bottle 20. In a further embodiment wherein the magnetic separation device comprises a container detachably secured to at least one magnetic sheet using a physical coupler therebetween, the container means is detachably secured to one magnetic sheet. However, the magnetic sheet is generally dimensionally coextensive in length, width, and shape to two or more sides of the container in forming magnetic separation device. More particularly, in an example of this further embodiment, the magnetic sheet may comprise a flexible magnetic sheet which may be applied as a "wrap" around a bottle such that the flexible magnetic sheet is generally dimensionally coextensive in length, width, and shape with two or more sides of the bottle, particularly in relation to the fluid holding chamber of the bottle. Also, where the bottle is cylindrical in shape, the flexible magnetic sheet could be applied as a "wrap" that covers all or a substantial portion of the circumference of the outer surface of the fluid chamber portion of the bottle. This variation of the embodiment is particularly useful for cell culture bottles which may then be placed in a roller apparatus and incubated with gentle rotation of the bottle.

EXAMPLE 3

Figure 6:
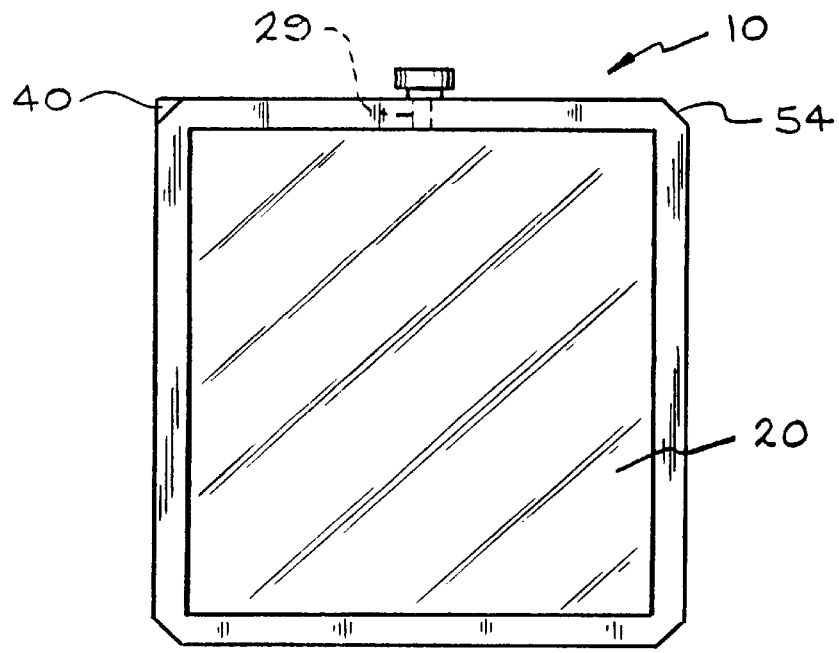
FIG. 6 is a plan view of a magnetic separation device, showing a magnetic sheet in relation to the container, which are contacted together using a physical coupler.

In another embodiment, the magnetic separation device comprises a frame, and a container which is removably attached to magnetic sheet by a physical coupler (see, e.g., FIGS. 6, 7A, and 7B). In a preferred embodiment, the frame is used to form the container. This construction is particularly useful for magnetic separation devices that are used in performing magnetic separations involving small volumes of fluid (e.g., 500 $\mu$l to 5 ml). Further, the frame of the magnetic separation device may serve as a support structure to which is clamped or held in contact with a support stand (e.g., slotted rack) in placing a magnetic separation device into the support stand. As will be apparent to one skilled in the art, placing the magnetic separation device into a support stand holds the magnetic separation device in a supported, stationary position, thereby facilitating the user to further manipulate the magnetic separation device including, but not limited to, in a filling process, or in stacking one or more magnetic separation devices for incubation or storage. In one variation of this embodiment, the magnetic separation device further comprises a backing plate which is placed in physical contact with the magnetic sheet on the side of the magnetic sheet opposite to that where the container is detachably secured (see, e.g., FIG. 7B). The composition, placement, and function of such a backing plate has been previously describe in detail in Example 2 herein.

In a further preferred construction as illustrated in FIGS. 6–7, magnetic separation device 10 comprises a two piece frame with frame pieces 54 and 56. The basic composition of the frame pieces may comprise suitable plastic, thermoplastic, synthetic, or natural materials which can be fabricated into a framework structure, thereby achieving the required structural integrity for its intended purpose. It is also desirable that the frame pieces lack ferromagnetic material in a location that would substantially detract magnetic particles placed in the chamber from being attracted to, and held into position by, a detachably secured magnetic sheet. As the specific character of the basic composition of the frame pieces does not in and of itself constitute the subject matter of the instant invention, it should be apparent to those skilled in the art that a wide latitude of choice can be exercised in selecting a material suitable for formation and/or fabrication of frame pieces 54 and 56. The dimensions of frame and the frame pieces depend on one or more factors including, but not limited to, the desired fluid capacity of the chamber (container) formed therewith, the dimensions of the container, and the dimensions of the magnetic sheet. Assembly of the frame can be achieved by methods known in the art that include, but are not limited to, pressing, sonic welding, adhesive bonding, and the like.

Placed and sealed in between frame pieces 54 and 56 is thin film 20. This can be achieved by any one of several processes. In referring to these processes, and the constructions depicted in the accompanying figures, it is noted that "upper" and "lower" are terms only used for purposes of ease of illustration and referencing. For example, thin film 20 may be sealed to the lower side of frame piece 54 by any one of several methods known in the art (e.g., heat-sealed, adhesive bonding, and the like) prior to the alignment with frame piece 56 and subsequent assembly. Alternatively, thin film 20 may be placed between frame pieces 54 and 56, the frame pieces are then aligned, and the assembly then sealed to sandwich thin film 20 between the frame pieces. In a further example, thin film 20 may be sealed to the upper surface of frame piece 56, whereas thin film 19 may be sealed to the lower surface of frame piece 56, the frame pieces are then aligned to form the frame, and the assembly then sealed. In a further example, thin film 19 and thin film 20 are co-extensive portions of the same sheet of thin film. Each of thin films 19 and 20 form a wall of the container of magnetic separation device 10, wherein into the chamber of the container is placed a fluid for magnetic separation. The composition of thin films 19 and 20 may be sheets of the same or similar material as described for the bags previously discussed herein in more detail. For example, the thin films may be of a thermoplastic polymer, of high ethylene vinyl acetate polymer content, a flexible synthetic resin, gas-permeable membrane, polyvinyl chloride, polyolefins, polyurethanes or other suitable material having properties compatible with its intended purpose.

As illustrated in FIGS. 7A and 7B, disposed on each of the lower and upper sides of frame piece 56, in a substantially parallel relationship and without any additional supporting structure therebetween, are thin films 19 and 20, respectively. In this construction, thin films 19 and 20 are spaced apart in a face-to-face relationship; thus a container is formed wherein the upper side of the container is formed by thin film 20, the lower side of the container is formed by thin film 19, side walls of the container are formed by inner surface 59 of frame piece 56, with a chamber comprising the open space bounded by thin films 19 and 20 and inner surface 59. It is within this chamber that the magnetic separation process occurs. Also illustrated in FIGS. 7A and 7B, frame piece 56 contains at least one aperture 29 (opening or channel) that is sealable so that a fluid can be delivered into or withdrawn from the chamber of magnetic separation device 10. The aperture can be in one of several forms known in the art. For example, one or more of frame pieces 54 and 56 may have one or more holes drilled therethrough providing one or more opening (e.g., apertures) to the chamber of the magnetic separation device. Each opening may then be filled and sealed with a material comprising a gasket that is sufficiently pliable to be self-sealing thereby allowing for penetration by a needle and resealing after needle withdrawal. Thus, in this embodiment, the fluid can be introduced into or withdrawn from magnetic separation device 10 using a conventional syringe and needle. In that regard, magnetic separation device 10 may further comprise at least one aperture comprising a vent port which may be used to vent out air from the chamber during the injection of sample into the chamber using the syringe and needle Alternatively, the inner surface 59 and/or frame piece 56 may comprise a material comprising a gasket that is sufficiently pliable to be self-sealing thereby allowing for penetration by a needle and resealing after needle withdrawal. Thus, in this embodiment, the fluid can be introduced into or withdrawn from magnetic separation device 10 using a conventional syringe and needle. In that regard, magnetic separation device 10 may further comprise at least one aperture comprising a vent port which may be used to vent out air from the chamber during the injection of sample into the chamber using the syringe and needle. In another alternative, aperture 29 may comprise an opening and channel of sufficient width to allow a micropipetor or a pipet to be inserted into and through the aperture in delivering a fluid into the chamber of magnetic separation device 10. Such an aperture is constructed in a manner such that the fluid can be directed into the chamber, without leaking of the fluid into other parts of the magnetic separation device. Conventional means may be used to open the aperture, and for closing the aperture in forming a "water-tight" seal. For example, wherein the aperture includes a neck portion, a removable cap may be used to seal off the aperture. In another example, a removable plug may be inserted into the aperture in sealing off the aperture.

As illustrated in FIGS. 7A and 7B, disposed on the lower side of thin film 19, in a substantially parallel relationship, detachably secured, and contacting a substantial portion of the lower side of thin film 19, is magnetic sheet 40 such that thin film 19 and magnetic sheet 40 meet in a face to face manner in being assembled together to form magnetic separation device 10. The magnetic sheet 40 and the lower side of thin film 19, may generally (but not necessarily) be dimensionally coextensive in length, width, and shape (especially in relation with the fluid holding chamber of magnetic separation device 10). A portion of magnetic sheet 40 may, but does not necessarily have to, extend beyond the dimensional margins of the two-piece frame formed by assembling frame pieces 54 and 56 (see, e.g., FIG. 6); or alternatively have a radially projecting portion, such as a tab. In either case, the projecting portion of magnetic sheet 40 may make easier the gripping of the magnetic sheet by the user to facilitate pulling apart or disengaging the magnetic sheet from the magnetic separation device. "Detachably secured to" may comprise (a) the magnetic sheet being detachably secured to a substantial portion of the lower surface of thin film 19 (e.g., by a non-permanent adhesive); (b) detachably secured to a limited portion of the lower surface of thin film 19 (e.g., a portion comprising the outer edges only, by a non-permanent adhesive, by a ferromagnetic material 53 as illustrated in FIGS. 7A and 7B, by one or more clamps, or by the like); (c) detachably secured over thin film 19 such as by detachably securing the magnetic sheet to any portion of the frame (e.g., to frame piece 56) in a manner that promotes contact between the magnetic sheet and the lower surface of thin film 19, particularly over that portion of thin film 19 which is involved in forming the fluid holding chamber; and (d) a combination thereof. In one exemplary embodiment, one or more additional magnetic sheets may be placed in physical contact with, and generally dimensionally co-extensive with, the detachably secured magnetic sheet on the side of the magnetic sheet which is opposite to the side contacting the container.

In another exemplary embodiment, positioned along (pressure fitted or embedded along, or bonded to) a surface of one or more of the frame pieces is a physical coupler comprising a ferromagnetic material (see, e.g., FIGS. 7A and 7B). The ferromagnetic material may be insulated from, or may be positioned so as to avoid possible magnetic interactions with, magnetic particles which are placed into the fluid holding chamber of the container of magnetic separation device 10. Thus, when magnetic sheet 40 is placed over thin film 19 in assembling magnetic separation device 10, magnetic sheet 40 is attracted to the ferromagnetic material 53 spaced or located along frame piece 56, thereby causing magnetic sheet 40 to come into functionally close proximity (including, but not limited to, contact; and sufficient for a magnetic separation process as described herein) with, and to be held in position in relation to, a substantial portion of thin film 19 (a surface of the container). In an additional embodiment, the magnetic separation device further comprises a backing plate which is placed in physical contact with the magnetic sheet on the side of the magnetic sheet opposite to that contacting thin film 19 (see, e.g., FIG. 7B). The backing plate is held into position by the magnetic attractive forces of magnetic sheet 40. Other details as to the composition, placement, and function of such a backing plate has been previously describe in Example 2 herein.

EXAMPLE 4

In this example, illustrated are various embodiments of the method according to the present invention for separating at least one subpopulation of a biological molecule of interest from a mixed population of biological molecules in a fluid by using the magnetic separation device according to the present invention. A first embodiment is a method of negative selection. In this first embodiment, the target biological molecules are separated from the fluid using the magnetic separation device according to the present invention. The fluid, depleted of the one or more subpopulations of target biological molecules ("one or more target biological molecules"), is then utilized for its intended purpose. The one or more target biological molecules are then discarded or otherwise disposed of. In a second embodiment, both negative selection and positive selection ("combination selection") are performed wherein the fluid, depleted of the one or more target biological molecules, is then utilized for its intended purpose, and the one or more isolated target biological molecules are used for their intended purpose(s).

A third embodiment is a method of positive selection using the magnetic separation device; i.e., the one or more biological molecules desired to be isolated from the fluid are isolated by positive selection. Positive selection involves separating the one or more target biological molecules from a mixed population of biological molecules present in a fluid, and then discarding the remaining unwanted (e.g., non-target) populations of biological molecules present in the fluid which are not magnetically separated. The objective of positive selection using the method and magnetic separation device according to the present invention is to isolate the one or more target biological molecules thereby obtaining relatively high yields and purity of the one or more target biological molecules. The magnetically separated one or more biological molecules may then be used for their intended purpose. Depending upon what the intended purpose is, the magnetically separated one or more biological molecules may be isolated in a manner in which all or a portion of the biological function is lost; or alternatively, may be isolated in a manner to substantially preserve biological functionality. For example, if the biological molecule is a specific cell type, and the intended purpose is to analyze that cell type by flow cytometer, it is not necessary that the cell maintain any or all of its biological function. Rather, the positively selected cells need only to retain the physical presence of the cell surface and/or internal component which is to be detected by flow cytometry. In contrast, if the target biological molecule is a cell type which is to be introduced into culture subsequent to separation, desirably the separated cells are substantially isolated in their native form; e.g., retaining substantially all of the biological function.

In general, the method of using the magnetic separation device according to the present invention involves obtaining a fluid containing a mixed population of biological molecules, from which it is desired to separate at least one subpopulation of biological molecules. For example, when a single subpopulation of biological molecules is desired to be isolated, the fluid from which it is to be isolated, and magnetic particles coated with a ligand (magnetic separation reagent) having sufficient binding specificity and affinity for the targeted subpopulation of biological molecule, are introduced into the container means of the magnetic separation device. Agitation means may be used to facilitate the contact between the magnetic separation reagent and the target biological molecule in forming complexes within the chamber of the container means. Alternatively, the fluid and magnetic separation reagent are mixed together first, and then introduced into the magnetic separation device, followed by agitation of the magnetic separation device. For example, if the container comprises a bag or a bottle, the magnetic separation device may be gently agitated either manually, or agitated automatically (e.g., using a rotator means or rocker means) by placement of the magnetic separation device onto the rotator or rocker means.

Figure 2:
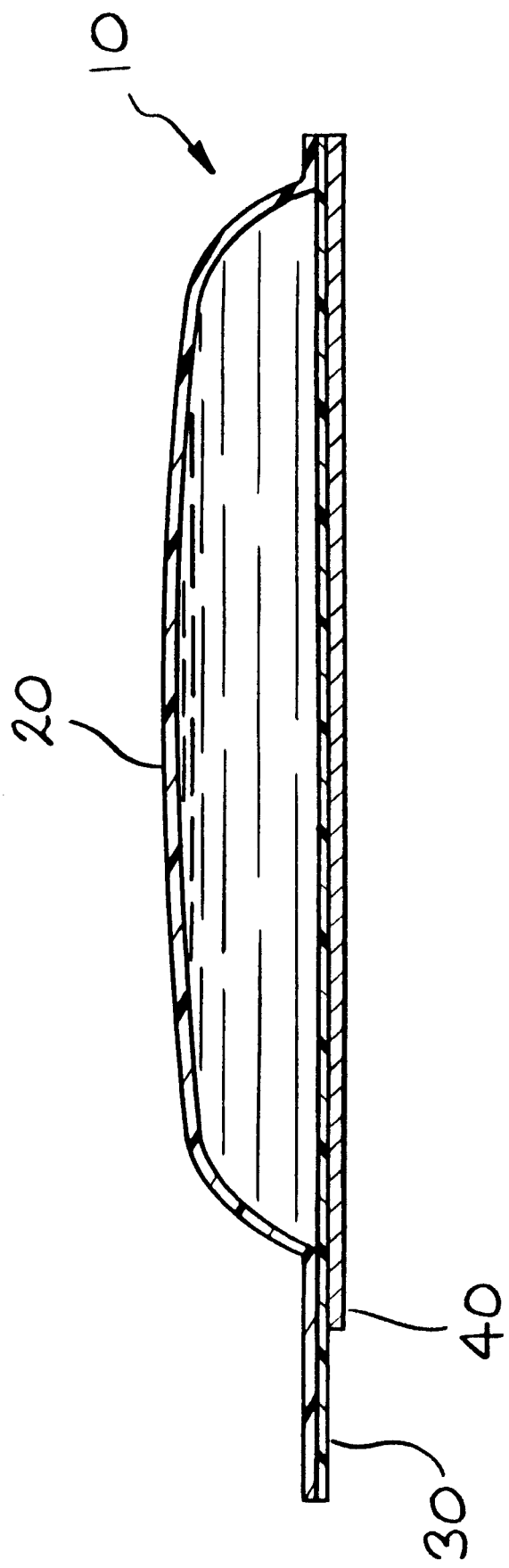
FIG. 2 is a side view in section of the magnetic separation device taken on line 2—2 of FIG. 1 showing the magnetic separation device lying on a flat surface.

In one embodiment, the magnetic separation device may be placed in a manner such that the magnetic sheet lies flat, and in contact with a supporting surface (see, e.g., FIG. 2 showing the magnetic sheet comprising a stiff magnetic sheet; and FIGS. 7A and 7B). In one variation of this embodiment, some or all of the magnetic separation reagent may be added first so as to already be substantially held into place along, and in physical contact with, the inside surface of the fluid holding chamber of the container adjacent to and along the dimensions of the magnetic sheet; and then the fluid is added to the magnetic separation device. Alternatively, the fluid and magnetic separation may be mixed first, and then the magnetic separation device may be placed in a manner such that the magnetic sheet lies flat, and in contact with a supporting surface. After a sufficient time, the magnetic separation reagent contacts and binds to the target biological molecule present in the fluid, thereby forming complexes. These complexes contact, and are held in position along, inside of the face of the container (along the fluid holding chamber), the outer surface of which is detachably secured to the magnetic sheet, because of the attraction to the magnetic field strength of the magnetic sheet. In either embodiment, or related embodiments, there is an incubation period which consists of a time period sufficient for contact and binding interactions between the magnetic separation reagent and the target biological molecule in forming complexes, and the binding of the complexes to the inside surface of the container means adjacent to and along the dimensions of the magnetic sheet. It is appreciated by those skilled in the art that the incubation period may vary depending on factors including, but not limited to, the magnetic field strength of the magnetic sheet, the amount of magnetic separation reagent relative to the amount of the target biological molecule present in the fluid, the type of magnetic particle used in forming the magnetic separation reagent, and the manner in which the incubation step is performed.

After the incubation period, the fluid is removed from the container, e.g., via the aperture. If negative selection is being performed, the fluid (and contents therein) thereby removed comprises the desired end product. If positive selection is being performed, the fluid may be discarded since the separated target biological molecule (complexed to the magnetic separation reagent) is the desired end product. In positive selection, the inner (interior) surfaces of the container (e.g., of the fluid holding chamber) of the magnetic separation device may be washed with a buffer or solution biologically compatible with the separated target biological molecule to remove any remaining unbound or nonspecifically bound biological molecules still present inside the container. In that regard, one or more washes may be performed by introducing the wash solution into the container via the aperture, gently agitating the magnetic separation device to rinse one or more inner surfaces (e.g., the interior surface of the container adjacent to and along the dimensions of the magnetic sheet, and to which is bound the complexes) and then removing the wash solution from the magnetic separation device via the aperture.

After the washing step of the positive selection process using the method according to the present invention, performed is a step in which the complexes are collected from the magnetic separation device. It will be apparent to those skilled in the art that the collection step may be performed in a number of ways. In general, the collection step involves introducing a final solution (e.g. a solution biologically compatible with the target biological molecule which is to be used for storing, and/or for use with, the target biological molecule) into the container of the magnetic separation device (e.g., via the aperture) such that the final solution is in physical contact with the complexes held into position by the magnetic sheet of the magnetic separation device; and then separating the magnetic sheet away from the container (e.g., by peeling the container away from the magnetic sheet, by peeling the magnetic sheet away from the container, or a combination thereof), thereby removing the magnetic force holding the complexes into place inside the container, and thereby releasing the complexes into the final solution contained within the fluid holding chamber. The final solution, containing the separated target biological molecule, may then be removed from the container (e.g., via the aperture), if desired.

If desired, the separated biological molecule may then be harvested from the complexes using an elution process known to those skilled in the art to depend on the type of chemical or molecular interaction between the ligand and the target biological molecule. As will be appreciated by those skilled in the art, whether elution is desirable or not will depend on factors which include, but are not limited to, the nature of the separated target biological molecule, and its intended use subsequent to the selection process. Elution processes include, but are not limited to, changing the pH; changing the salt concentration; adding a molecule which can compete with the separated biological molecule for binding to the ligand of the magnetic separation reagent; or adding an agent which alters the conformation of the ligand or the target biological molecule, or both; such that the separated target biological molecule is dissociated from the ligand. In one embodiment in which a degradable magnetic particle is used as a component in the magnetic separation reagent, a elution process to separate the separated target biological molecule from the magnetic particle may be obviated upon degradation of the magnetic particle. In another embodiment in which the container comprises a cell culture bag, and the separated target biological molecule is a living cell of a desired cell type, the final solution may comprise growth medium compatible for growth of the separated cell type. In this particular embodiment, it is not necessary to remove the cells and growth medium from the container. Rather, the container, containing the growth medium and separated cell type, may be placed directly into an incubator supplying conditions (temperature, atmospheric) sufficient for cell growth. For many cell types, an elution process is not necessary as these cells, when attached to a magnetic particle, will still divide to form new cells during the growth process, as will be apparent from the following embodiments.

It will be appreciated by those skilled in the art that the above-described method according to the present invention may be modified. For example, using the above-described method and magnetic separation device, instead of separating a single subpopulation of biological molecules from mixed populations of biological molecules, simultaneously separated from the fluid are more than one distinct subpopulations of target biological molecules. In one variation of this example, the magnetic separation reagent comprises (a) magnetic particles coated with a single type of ligand having multiple binding specificities (e.g., for more than one subpopulation of biological molecule); (b) magnetic particles coated with more than one type of ligand, each type of ligand differing in the binding specificity as compared to the other, thereby together binding more than one subpopulation of target biological molecule; (c) a series of magnetic particles wherein each representative species of the series is coated with a ligand having a binding specificity for a single subpopulation of target biological molecule and which is different from the binding specificity of other species in the series; and a combination thereof. Thus, by adding such a magnetic separation reagent to the fluid, and using the method and device according to the present invention, multiple distinct subpopulations of target biological molecules may be separated simultaneously from the fluid.

There are several variations by which multiple subpopulations of biological molecules may be targeted, and isolated from a fluid containing mixed populations of biological molecules, using the method and magnetic separation device according to the present invention. For brevity, the method for separating multiple subpopulations of biological molecules will mainly be described in terms of separately isolating two distinct subpopulations of target biological molecules from mixed populations of biological molecules contained in a fluid. It will be apparent from this description that the magnetic separation device and the method of using the same may be used to isolate (separately or simultaneously) more than two distinct subpopulations of target biological molecules from mixed populations of biological molecules contained in a fluid. Thus, it should be understood that the magnetic separation device and the method of using the same according to the present invention may also be used to isolate more than two distinct subpopulations of target biological molecules from mixed populations of biological molecules contained in a fluid. Two or more distinct subpopulations of target biological molecules may be isolated in a single magnetic separation device; or may be separated using a series of magnetic separation devices which are physically connected in tandem, but which can be manipulated to maintain a separate container per magnetic separation device. Each magnetic separation device, in a series of magnetic separation devices, may also have at least one separate aperture specific for each respective container.

For example, to separately isolate two distinct subpopulations of target biological molecules from mixed populations of biological molecules contained in a fluid, performed are sequential isolations thereby separating the distinct subpopulations of target biological molecules one at a time. In one illustration of this example, reference is made to FIG. 5 which shows a magnetic separation device 10 comprising container 20 detachably secured by a physical coupler comprising non-permanent adhesive 45 to magnetic sheets 40 and 41. In continuing with this illustration, magnetic separation device 10 is turned on its side such that magnetic sheet 40 is lying substantially flat in relation to, and in physical contact with, a support surface. Introduced into container 20, via aperture 29, is a first magnetic separation reagent having binding specificity for a first target biological molecule such that the first magnetic separation reagent becomes substantially held into place along, and in physical contact with, the inside surface (i.e., interior surface of the fluid holding chamber) of face 30 of container 20, and adjacent to and along the dimensions of magnetic sheet 40. After the first magnetic separation reagent is held into place as such, the magnetic separation device is rotated approximately 90 degrees such that now only magnetic sheet 41 is lying substantially flat in relation to, and in physical contact with, the support surface. Introduced into container 20, via aperture 29, is a second magnetic separation reagent having binding specificity for a second target biological molecule such that the second magnetic separation reagent becomes substantially held into place along, and in physical contact with, the inside surface (i.e., interior surface of the fluid holding chamber) of face 31 of container 20, and adjacent to and along the dimensions of magnetic sheet 41. The result to this point is magnetic separation device 10 having bound onto one inner surface the first magnetic separation reagent, and having bound onto another inner surface the second magnetic separation reagent. Now, the fluid having a mixed population of biological molecules, from which is to be isolated the first and second target biological molecules, is introduced into container 20 (e.g., via aperture 29) of magnetic separation device 10. Magnetic separation device 10 is placed on its side, and substantially flat, and then gently rotated from side to side such that physical contact by the fluid is alternated between the bound first magnetic separation reagent and the bound second magnetic reagent. For example, magnetic separation device 10 is first positioned such that magnetic sheet 40 is lying substantially flat in relation to, and in physical contact with, the support surface. The fluid is then in contact with substantially only the first magnetic separation reagent (along inner surface of face 30). The magnetic separating device is then rotated 90 degrees such that the fluid is then in contact with substantially only the second magnetic separation reagent (along inner surface of face 31). The rotation of the magnetic separation device 10 may be continued for a sufficient time such that the first magnetic separation reagent contacts and binds to the first target biological molecule present in the fluid, thereby forming a first set of complexes; and the second magnetic separation reagent contacts and binds to the second target biological molecule present in the fluid, thereby forming a second set of complexes. The first set of complexes contact, and are held in position along, the inner surface of face 30; whereas the second set of complexes contact, and are held in position along, the inner surface of face 31. The fluid is then removed from container 20 (e.g., via aperture 29). If negative selection is being performed, the fluid (and contents therein) thereby removed comprises the desired end product. If positive selection is being performed, the fluid may be discarded, since the two separated target biological molecules (held in their respective positions in the fluid holding chamber of container 20) are the desired end products. In positive selection, the inner surfaces of the container (e.g., the fluid holding chamber) of the magnetic separation device may be washed with a buffer or solution biologically compatible with the separated target biological molecules to remove any remaining unbound or nonspecifically bound (e.g., non-target) biological molecules still present inside the container. In that regard, one or more washes may be performed by introducing a wash solution into the magnetic separation device via the aperture, gently agitating the container to rinse the inner (inside) surfaces of the container (and thus also contacting, and washing both the first and second sets of complexes held in their respective positions). After each wash step, the wash solution is removed from the container (e.g., via the aperture).

After the washing step of the positive selection process using the method according to the present invention, performed is a collection step in which the first and second sets of complexes are separately collected from the magnetic separation device. It will be apparent to those skilled in the art that the collection step may be performed in a number of ways. In continuing with this particular illustration, the collection step involves introducing a first final solution (e.g. a solution biologically compatible with the first target biological molecule which is to be used for storing, and/or for use with, the first target biological molecule) into the magnetic separation device (e.g., via the aperture) such that the first final solution is in substantial physical contact with the first set of complexes held into position by magnetic sheet 40 of the magnetic separation device. Magnetic sheet 40 is then disengaged from container 20 (e.g., by an action selected from the group consisting of gripping the container and pulling it apart and away from the magnetic sheet, gripping the magnetic sheet and pulling it apart and away from the container, or a combination thereof) thereby removing the magnetic force holding the first set of complexes into place in the magnetic separation device, and thereby releasing the first set of complexes into the first final solution contained within the fluid holding chamber. The first final solution, containing the separated first target biological molecule, may then be removed from the magnetic separation device (e.g., via the aperture). Optionally, a second wash step may be performed to substantially remove any traces of the first target biological molecule before the collection step proceeds to the process of removing the second set of complexes (containing the separated second target biological molecule).

In continuing with this illustration of the collection step, a second final solution (e.g. a solution biologically compatible with the second target biological molecule which is to be used for storing, and/or for use with, the second target biological molecule) is introduced into the magnetic separation device (e.g., via the aperture) such that the second final solution is in substantial physical contact with the second set of complexes held into position by magnetic sheet 41 of the magnetic separation device. Magnetic sheet 41 is then disengaged from container 20 (e.g., by a pulling action selected from the group consisting of gripping the container and pulling it apart and away from the magnetic sheet, gripping the magnetic sheet and pulling it apart and away from the container, or a combination thereof) thereby removing the magnetic force holding the second set of complexes into place in the magnetic separation device, and thereby releasing the second set of complexes into the second final solution contained within the fluid holding chamber. The second final solution, containing the separated second target biological molecule, may then be removed from the container (e.g., via the aperture). As already described in detail herein, if desirable, the separated first target biological molecule or the separated second target biological molecule may then be harvested from their respective complexes using an elution process known to those skilled in the art.

EXAMPLE 5

Presented in this example are illustrations of the functioning of the magnetic separation device according to the present invention. Into a volume of 20 ml of phosphate buffered saline (PBS) was suspended $10^6$ magnetic particles/ml of a commercially available magnetic particle (DYNABEAD M-450 coated with a polymer and avidin). The 20 ml suspension was then introduced into a magnetic separation device similar to that illustrated in FIG. 1. The magnetic separation device, containing the suspension, was turned on its side such that the magnetic sheet was lying substantially flat in relation to, and in physical contact with, a support surface. In such a position and with gentle agitation, the magnetic separation device was incubated at room temperature for 5 minutes. After the incubation, the fluid was removed from the magnetic separation device. For determining the percentage of magnetic particles retained in the magnetic separation device, an aliquot of the removed fluid was placed in a hemacytometer, and the magnetic particles were counted using a light microscope. The results indicated that the removed solution contained less than one magnetic particle per ml of solution. Thus, less than 0.0001% of the magnetic particles were lost in a negative selection process using the magnetic separation device according to the present invention.

In another illustration, a suspension comprising 20 ml of PBS and $2\times10^7$ particles ($10^6$ particles/ml) was introduced into a magnetic separation device, the magnetic separation device was then turned on its side such that the magnetic sheet was lying substantially flat in relation to, and in physical contact with, a support surface. In such a position and with gentle agitation, the magnetic separation device was incubated at room temperature for 5 minutes. After the incubation, the fluid was removed from the magnetic separation device. A wash was performed by introducing a wash solution (20 ml PBS) into the container portion of the magnetic separation device, gently agitating the magnetic separation device for 30 seconds, and then removing the wash solution. Two additional wash steps were performed in the same manner. A final solution (20 ml PBS) was then introduced into the magnetic separation device, the magnetic sheet was peeled away and removed from contact with the container, and the container was then gently agitated for a few minutes. For determining the percentage of magnetic particles recovered in the final solution, an aliquot of the removed final solution was placed in a hemacytometer, and the magnetic particles were counted using a light microscope. The results indicated that the removed final solution contained $8.5\times10^5$ magnetic particles/ml (total of $1.7\times10^7$ magnetic particles). Thus, 85% of the magnetic particles were recovered in a positive selection process using the magnetic separation device according to the present invention.

EXAMPLE 6

Presented in this example are further illustrations of the functioning of the magnetic separation device according to the present invention. In one illustration, a positive selection of a specific subpopulation of cells was performed. The cells were SW620, a human colorectal carcinoma cell line (expressing cell surface Ber-EP4 antigen), and the magnetic separation reagent comprised anti-Ber-EP4 antibody-coated particles (purchased commercially). A suspension was created by mixing approximately $1\times10^7$ SW620 cells in 1 ml of PBS with approximately $1\times10^7$ (15 $\mu$l of commercial preparation) of anti-Ber-EP4 antibody-coated particles. The suspension was then incubated a room temperature for 30 minutes with mixing by gentle agitation. The suspension was then diluted to a total volume of 20 ml by the addition of PBS. The magnetic separation device was inflated by the injection of 180 ml of sterile air into its chamber (e.g., using a syringe with a 0.2 $\mu$m syringe filter). The magnetic separation device was positioned such that the magnetic sheet portion was on top with reference to the user's view of the magnetic separation device. The suspension containing the SW620 cells and magnetic separation reagent was then carefully injected into the chamber of the magnetic separation device onto and along the opposite inner side of the chamber (e.g., the inner side across the chamber from the magnetic sheet). The magnetic separation device was then inverted such that the suspension containing the SW620 cells and magnetic separation reagent became in contact with the inner surface of the chamber adjacent to the magnetic sheet. The magnetic separation device was then placed onto a support surface in that position such that the magnetic sheet was lying substantially flat in relation to, and in physical contact with, a support surface (e.g., see FIG. 2).

In such a position and, with gentle agitation, the magnetic separation device was incubated at room temperature for 5 minutes. After the incubation, the fluid was removed from the magnetic separation device. A wash was performed by introducing a wash solution (20 ml PBS) into the chamber of the magnetic separation device (e.g., via an aperture), gently agitating the magnetic separation device for 30 seconds, and then removing the wash solution. An additional wash step was performed in the same manner. A final solution comprising 50 ml of culture medium (Dulbecco's Minimal Essential Medium (DMEM) with 10% fetal calf serum) was then introduced into the magnetic separation device; the magnetic sheet was separated and removed from contact with the container; and the container was then gently agitated for a few minutes to mix the media with remaining complexes of SW620 bound to magnetic separation reagent. A small aliquot of the medium was then removed, and placed in a hemacytometer, and the number of SW620 cells remaining after positive selection were counted under light microscopy. The number of SW620 cells remaining after positive selection were compared to the number of SW620 cells introduced into the magnetic separation device at the beginning of the positive selection process. The results indicated that greater than 70% of the SW620 cells were recovered in a positive selection process using the magnetic separation device according to the present invention, and a commercial source of magnetic separation reagent. The remaining portion of the positively separated SW620 cells, while still complexed to the magnetic separation reagent at the initiation of culture, were cultured in the container for several days in a culture incubator at 37° C. at 5% $CO_2$. After 6 days of culture, SW620 cells were removed and counted. The results indicated that the culture contained about $6\times10^7$ SW620 cells in 50 ml with a cell viability of about 82%.

In another illustration, a positive selection of a specific subpopulation of cells from a mixed population of cells was performed. In this illustration, the subpopulation of cells were CD4+ lymphocytes, the mixed population of cells were white blood cells, and the magnetic separation reagent comprised anti-CD4 antibody-coated particles (purchased commercially). A white blood cell-enriched preparation ("WBCs") was purchased commercially. The WBCs were then treated with a solution containing ammonium chloride to ensure lysis of any remaining red blood cells. A suspension of WBCs was then created by mixing approximately $2\times10^7$ WBCs in 440 $\mu$l of PBS with the magnetic separation reagent (approximately $8\times10^7$ anti-CD4 antibody-coated particles in 560 $\mu$l). The suspension was then diluted to a total volume of 20 ml by the addition of PBS. The magnetic separation device was inflated by the injection of sterile air into its chamber. The magnetic separation device was positioned such that the magnetic sheet portion was on top with reference to the user's view of the magnetic separation device. The suspension containing the WBCs and magnetic separation reagent was then carefully injected into the chamber onto and along the opposite inner side of the chamber (e.g., the inner side of the chamber across from the magnetic sheet). The magnetic separation device was then inverted such that the suspension containing the WBCs and magnetic separation reagent became in contact with the inner surface of the chamber adjacent to the magnetic sheet. Maintaining that position, the magnetic separation device was then placed onto a support surface such that the magnetic sheet was lying substantially flat in relation to, and in physical contact with, a support surface (e.g., see FIG. 2). In such a position, and with gentle agitation, the magnetic separation device was incubated at 4° C. for 60 minutes with mixing by gentle agitation. After the incubation, the fluid was removed from the magnetic separation device. A wash was performed by introducing a wash solution (20 ml PBS) into the chamber of the magnetic separation device, gently agitating the magnetic separation device for 30 seconds, and then removing the wash solution. Three additional wash steps were performed in the same manner. A final solution comprising 50 ml of culture medium (RPMI with 10% fetal calf serum) was then introduced into the magnetic separation device; the magnetic sheet separated from contact with the container; and the container was then gently agitated for a few minutes to mix the media with remaining complexes of cells bound to magnetic separation reagent. A small aliquot of the medium was then removed, stained for flow cytometric analysis using anti-CD4 monoclonal antibody labeled to fluorscein isothiocyanate (FITC). Analysis by flow cytometry indicated that about 90% or greater of the cells recovered by the positive selection process were CD4+ cells. Thus, the magnetic separation device according to the present invention may be used for efficient separation of a specific subpopulation of cells from a mixed population of cells. The remaining portion of the positively separated CD4+ cells, while still complexed to the magnetic separation reagent at the initiation of culture, were cultured in the container in a culture incubator at 37° C. at 5% $CO_2$. After 2.5 days in culture, the cells were removed, and counted. The results indicated that the culture contained about $1 \times 10^7$ cells with a cell viability of about 75%.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. A magnetic separation device for separation of one or more biological molecules in a fluid comprising: a container comprising a chamber capable of holding the fluid; a magnetic sheet; and a physical coupler to detachably secure the magnetic sheet and an outer surface of the container together in a face to face manner in assembling a unit; wherein the assembled unit comprises the magnetic separation device.

2. The magnetic separation device of claim 1, wherein the outer surface comprises a flat surface.

3. The magnetic separation device of claim 2, wherein the magnetic sheet and the outer surface of the container to which it is detachably secured are generally dimensionally coextensive in length, width, and shape.

4. The magnetic separation device of claim 1, wherein the physical coupler comprises a ferromagnetic material.

5. The magnetic separation device of claim 1, wherein the physical coupler comprises a non-permanent adhesive.

6. The magnetic separation device of claim 5, wherein the non-permanent adhesive coats an outer surface of the container that comes in contact with the magnetic sheet in detachably securing the magnetic sheet to the container.

7. The magnetic separation device of claim 5, wherein the non-permanent adhesive coats a face of the magnetic sheet which then contacts the container in detachably securing the magnetic sheet to the container.

8. The magnetic separation device of claim 5, wherein the non-permanent adhesive coats both the outer surface of the container and a face of the magnetic sheet, wherein the adhesive-coated outer surface and the adhesive-coated face are contacted together in detachably securing the magnetic sheet to the container.

9. The magnetic separation device of claim 1, wherein the magnetic sheet is flexible.

10. The magnetic separation device of claim 1, wherein the magnetic sheet is substantially stiff.

11. The magnetic separation device of claim 1, wherein the magnetic separation device further comprises a backing plate, wherein the backing plate is placed in physical contact with the magnetic sheet on the side of the magnetic sheet opposite to that to which is detachably secured the container.

12. The magnetic separation device of claim 1, wherein the magnetic separation device comprises a single unit.

13. The magnetic separation device of claim 1, wherein the magnetic separation device comprises a multiple unit, wherein the multiple unit comprises a plurality of the magnetic separation devices physically connected in tandem.

14. The magnetic separation device of claim 13, wherein a first magnetic separation device of the multiple unit has a magnetic sheet of a field strength which is different from the field strength of a magnet sheet of a second magnetic separation device of the multiple unit.

15. The magnetic separation device of claim 1, wherein an aperture of the container comprises a combination of an inlet and an outlet.

16. The magnetic separation device of claim 15, wherein the the container further comprises an aperture comprising a venting port for releasing air from the chamber.

17. The magnetic separation device of claim 1, wherein the magnetic sheet further comprises a tab means.

18. The magnetic separation device of claim 1, wherein the container comprises a bag.

19. The magnetic separation device of claim 18, wherein the bag is comprised of at least one wall comprised of a gas-permeable membrane.

20. The magnetic separation device of claim 18, wherein a portion of the bag extends beyond the dimensional margins of the detachably secured magnetic sheet, and wherein the extended portion of the bag is accessible for gripping by a user.

21. The magnetic separation device of claim 1, wherein the container is selected from the group consisting of a bottle, and a flask.

22. The magnetic separation device of claim 21, wherein the container comprises a bottle; wherein the bottle is cylindrical in shape; and wherein the magnetic sheet is applied to cover all or a substantial portion of an outer surface of the bottle which surrounds the chamber.

23. The magnetic separation device of claim 1, further comprising a container having detachably secured thereto, in a face to face manner, multiple magnetic sheets; wherein to more than one of a plurality of outer surfaces of the container is detachably secured a magnetic sheet.

24. The magnetic separation device of claim 23, wherein each of the multiple magnetic sheets is generally dimensionally coextensive in length, width, and shape to the outer surface of the container to which the magnetic sheet is detachably secured.

25. The magnetic separation device of claim 23, wherein the magnetic separation device comprises a single unit.

26. The magnetic separation device of claim 23, wherein the magnetic separation device comprises a multiple unit, wherein the multiple unit comprises a plurality of the magnetic separation devices physically connected in tandem.

27. The magnetic separation device of claim 23, wherein the magnetic separation device comprises a multiple unit, wherein the multiple unit comprises the magnetic separation device and a plurality of containers physically connected in tandem.

28. The magnetic separation device of claim 23, wherein each of the multiple flexible magnetic sheets further comprises a tab means.

29. The magnetic separation device of claim 23, wherein the physical coupler comprises a non-permanent adhesive which is used to detachably secure the container to the multiple magnetic sheets.

30. The magnetic separation device of claim 29, wherein the non-permanent adhesive coats a face of each of the multiple magnetic sheets.

31. The magnetic separation device of claim 29, wherein the non-permanent adhesive coats a combination of the more than one outer surface of the container, and a face of each of the multiple magnetic sheets.

32. The magnetic separation device of claim 23, wherein the container comprises a bag means.

33. The magnetic separation device of claim 23, wherein the container is selected from the group consisting of a bottle, and a flask.

34. The magnetic separation device of claim 23, wherein the physical coupler is a ferromagnetic material.

35. The magnetic separation device of claim 1, further comprising a container having detachably secured thereto, in a face to face manner, a single magnetic sheet; wherein more than one outer surface of the container has detachably secured thereto the single magnetic sheet.

36. The magnetic separation device of claim 35, wherein the physical coupler is a non-permanent adhesive that coats the more than one outer surface of the container.

37. The magnetic separation device of claim 35, wherein the physical coupler is a non-permanent adhesive that coats the face of the magnetic sheet.

38. The magnetic separation device of claim 35, wherein the physical coupler is a non-permanent adhesive that coats a combination of the more than one outer surface of the container, and the face of the magnetic sheet.

39. The magnetic separation device of claim 35, wherein the physical coupler is a ferromagnetic material.

40. The magnetic separation device of claim 1, wherein the container comprises at least one wall comprising a gas-permeable membrane.

41. The magnetic separation device of claim 1, wherein the container comprises at least two walls contacting a frame.

42. The magnetic separation device of claim 41, wherein the frame comprises two frame pieces.

43. The magnetic separation device of claim 41, wherein the container comprises at least one wall comprising a gas-permeable membrane.

44. The magnetic separation device of claim 41, wherein the frame is further used to contact, and place the magnetic separation device into, a support stand in holding the magnetic separation device in a stationary position.

45. The magnetic separation device of claim 41, wherein the magnetic sheet is flexible.

46. The magnetic separation device of claim 41, wherein the magnetic sheet is substantially stiff.

47. The magnetic separation device of claim 41, wherein the magnetic separation device further comprises a backing plate, wherein the backing plate is placed in physical contact with the magnetic sheet on the side of the magnetic sheet opposite to that to which is detachably secured the container.

48. The magnetic separation device of claim 42, wherein along a surface of at least one of the frame pieces is positioned a physical coupler comprising a ferromagnetic material.

49. The magnetic separation device of claim 42, wherein at least one of the frame pieces comprises a gasket material.

50. The magnetic separation device of claim 49, wherein the gasket material comprises the inner surface of the at least one frame piece.

51. The magnetic separation device of claim 42, wherein at least one of the frame pieces has one or more apertures.

52. The magnetic separation device of claim 51, wherein the one or more apertures is sealed with a gasket material.

53. A method for making the magnetic separation device according to claim 1 comprising detachably securing the container to the magnetic sheet, in a face to face manner, with a physical coupler in forming the magnetic separation device.

54. The method according to claim 53, wherein the physical coupler comprises a non-permanent adhesive, and the method comprises:

(a) applying the non-permanent adhesive in coating a surface selected from the group consisting of an outer surface of the container, a face of the magnetic sheet, or a combination thereof;

(b) contacting the outer surface of the container and the face of the magnetic sheet in a face to face manner; and (c) applying pressure to the container and magnetic sheet where they are dimensionally coextensive to detachably secure the container to the magnetic sheet in forming the magnetic separation device.

55. The method according to claim 54, wherein the container comprises a bag.

56. The method according to claim 54, wherein the container is selected from the group consisting of a bottle, and a flask; and wherein the container has at least one aperture.

57. The method according to claim 53, wherein the container further comprises a frame comprising two frame pieces.

58. The method according to claim 57, wherein the physical coupler comprises ferromagnetic material, and the method comprises:

(a) positioning the ferromagnetic material along a surface of at least one of the frame pieces to which is to be contacted the magnetic sheet;

(b) contacting the magnetic sheet to the ferromagnetic material thereby causing the magnetic sheet to be held in position, by magnetic attraction to the ferromagnetic material, and in functional close proximity to, a surface of the container in forming the magnetic separation device.

59. A method of using the magnetic separation device according to claim 1 for separating by positive selection a subpopulation of biological molecules present in a fluid containing a mixed population of biological molecules, the method comprising the steps of:

(a) obtaining the fluid containing a mixed population of biological molecules;

(b) mixing the fluid containing the mixed population of biological molecules with a magnetic separation reagent having sufficient binding specificity and affinity for the subpopulation of biological molecules;

(c) contacting the mixture from step (b) with the fluid holding chamber of the container of the magnetic separation device;

(d) incubating for a sufficient time for the magnetic separation reagent to contact and bind to the subpopulation of biological molecules thereby forming complexes, if the subpopulation of biological molecules is present;

(e) placing the magnetic separation device in a manner such that the magnetic sheet lies flat, and in contact with a supporting surface thereby allowing complexes formed to be held in position because of magnetic attraction of the magnetic separation reagent to the magnetic sheet;

(f) removing the fluid from the container;

(g) performing at least one wash step, wherein the wash step comprises adding a wash solution to the container and rinsing inner surfaces of the fluid holding chamber with the wash solution, and removing the wash solution from the container; and (h) performing a collection step, wherein the collection step comprises introducing a final solution into the container, disengaging the magnetic sheet away from the container, thereby releasing the complexes containing the separated subpopulation of biological molecules into the final solution.

60. The method according to claim 59, wherein the fluid containing the mixed population of biological molecules, and the magnetic separation reagent are mixed prior to introduction into and contact with the chamber of the container of the magnetic separation device.

61. The method according to claim 59, wherein the fluid containing the mixed population of biological molecules, and the magnetic separation reagent are each separately introduced into, and then mixed inside the chamber of the container of the magnetic separation device.

62. The method according to claim 59, wherein more than one wash step is performed.

63. The method according to claim 59, further comprising an elution step after step (h), wherein the elution step comprises eluting the separated subpopulation of biological molecules from the magnetic separation reagent by treating the complexes to dissociate the biological molecules from the magnetic separation reagent.

64. The method according to claim 59, wherein the subpopulation of biological molecules comprises a subpopulation of cells.

65. A method of using the magnetic separation device according to claim 23 for separating by positive selection multiple subpopulations of biological molecules present in a fluid containing a mixed population of biological molecules, the method comprising the steps of:

(a) obtaining the fluid containing a mixed population of biological molecules;

(b) adding a first magnetic separation reagent, having binding specificity for a first subpopulation of biological molecules to be separated, into the container of the magnetic separation device;

(c) placing the magnetic separation device in a manner such that a first magnetic sheet lies flat, and in contact with a supporting surface, and for a sufficient time in which the first magnetic separation reagent is bound in position in the container because of its magnetic attraction to the first magnetic sheet;

(d) rotating the position of the magnetic separation device in a manner such that a second magnetic sheet lies flat, and in contact with the supporting surface;

(e) adding a second magnetic separation reagent, having binding specificity for a second subpopulation of biological molecules to be separated, into the container of the magnetic separation device so that the second magnetic separation reagent is bound in position in the container because of its magnetic attraction to the second magnetic sheet;

(f) adding the fluid containing the mixed population of biological molecules into the container;

(g) gently rotating the magnetic separation device from side to side such that physical contact by the fluid is alternated between the first bound magnetic separation reagent and the second bound magnetic separation reagent, and incubating for a sufficient time for the first bound magnetic separation reagent to contact and bind to the first subpopulation of biological molecules to be separated thereby forming a first set of complexes, and for the second bound magnetic separation reagent to contact and bind to the second subpopulation of biological molecules to be separated thereby forming a second set of complexes;

(h) removing the fluid from the container;

(i) performing at least one wash step, wherein the wash step comprises adding a wash solution to the container and rinsing inner surfaces of the fluid holding chamber with the wash solution, and removing the wash solution from the container;

(j) performing a first collection step, wherein the first collection step comprises introducing a first final solution into the container, disengaging the first magnetic sheet away from the container, thereby releasing the first set of complexes containing the first separated subpopulation of biological molecules into the first final solution, and removing the first final solution containing the first set of complexes from the container; and (k) performing a second collection step, wherein the second collection step comprises introducing a second final solution into the container, disengaging the second magnetic sheet away from the container, thereby releasing the second set of complexes containing the second separated subpopulation of biological molecules into the second final solution, and removing the second final solution containing the second set of complexes from the container.

66. The method according to claim 65, wherein the more than one wash step is performed.

67. The method according to claim 65, further comprising an elution step, wherein the complexes are selected from the group consisting of the first set of complexes, the second set of complexes, and the first set of complexes and the second set of complexes; and wherein the complexes are treated to dissociate the separated subpopulation of biological molecules from the magnetic separation reagent.

68. The method according to claim 65, wherein the subpopulations of biological molecules comprise subpopulations of cells.

69. A method of using the magnetic separation device according to claim 1 for separating by negative selection a subpopulation of biological molecules present in a fluid containing a mixed population of biological molecules, the method comprising the steps of:

(a) obtaining the fluid containing a mixed population of biological molecules;

(b) mixing the fluid containing the mixed population of biological molecules with a magnetic separation reagent having sufficient binding specificity and affinity for the subpopulation of biological molecules to be removed;

(c) contacting the mixture from step (b) with the fluid holding chamber of the container of the magnetic separation device;
(d) incubating for a sufficient time for the magnetic separation reagent to contact and bind to the subpopulation of biological molecules thereby forming complexes, if the subpopulation of biological molecules is present;
(e) placing the magnetic separation device in a manner such that the magnetic sheet lies flat, and in contact with a supporting surface thereby allowing complexes formed to be held in position because of magnetic attraction of the magnetic separation reagent to the magnetic sheet; and
(f) removing the fluid from the container, wherein the fluid is depleted of the subpopulation of biological molecules to be removed.

70. The method according to claim 69, wherein the fluid containing the mixed population of biological molecules, and the magnetic separation reagent are mixed prior to introduction into and contact with the chamber of the container of the magnetic separation device.

71. The method according to claim 69, wherein the fluid containing the mixed population of biological molecules, and the magnetic separation reagent are each separately introduced into, and then mixed inside the chamber of the container of the magnetic separation device.

72. The method according to claim 69, wherein the subpopulation of biological molecules comprises a subpopulation of cells.

* * * * *